US010406362B2

(12) United States Patent
Famm et al.

(10) Patent No.: US 10,406,362 B2
(45) Date of Patent: Sep. 10, 2019

(54) NEUROMODULATION DEVICE

(71) Applicants: GALVANI BIOELECTRONICS LIMITED, Brentford, Middlesex (GB); HUNTINGTON MEDICAL RESEARCH INSTITUTES, Pasadena, CA (US); UNIVERSITY OF CHILE, Santiago (CL)

(72) Inventors: Hans Jakob Kristoffer Famm, Stevenage (GB); Hernan E. Lara, Santiago (CL); Victor Eugene Pikov, Stevenage (GB); Arun Sridhar, Stevenage (GB)

(73) Assignee: Galvani Bioeletronics Limited, Brentford, Middlesex (GB)

( * ) Notice: Subject to any disclaimer, the term of this patent is extended or adjusted under 35 U.S.C. 154(b) by 0 days.

(21) Appl. No.: 15/551,592

(22) PCT Filed: Feb. 19, 2016

(86) PCT No.: PCT/IB2016/050908
§ 371 (c)(1),
(2) Date: Aug. 16, 2017

(87) PCT Pub. No.: WO2016/132330
PCT Pub. Date: Aug. 25, 2016

(65) Prior Publication Data
US 2018/0043155 A1 Feb. 15, 2018

Related U.S. Application Data

(60) Provisional application No. 62/118,521, filed on Feb. 20, 2015.

(51) Int. Cl.
*A61N 1/36* (2006.01)
*A61F 7/12* (2006.01)
(Continued)

(52) U.S. Cl.
CPC .............. *A61N 1/3606* (2013.01); *A61F 7/12* (2013.01); *A61N 1/0551* (2013.01); *A61N 1/20* (2013.01);
(Continued)

(58) Field of Classification Search
CPC .............. A61N 1/3606; A61N 1/36107; A61N 1/36007; A61N 1/36135
See application file for complete search history.

(56) References Cited

U.S. PATENT DOCUMENTS

2015/0051594 A1\* 2/2015 Sobotka ............. A61N 1/36057
606/21
2016/0128767 A1\* 5/2016 Azamian ............ A61B 18/1492
606/41

FOREIGN PATENT DOCUMENTS

| WO | 02092165 A1 | 11/2002 |
| WO | 2009058258 A1 | 5/2009 |
| WO | 2013134548 A2 | 9/2013 |

OTHER PUBLICATIONS

International Search Report for International Application No. PCT/IB2016/050908, dated May 23, 2016.
(Continued)

*Primary Examiner* — Tammie K Marlen
(74) *Attorney, Agent, or Firm* — Alice P. Bradney

(57) ABSTRACT

Methods for treating polycystic ovarian syndrome with a neuromodulation device that modulates sympathetic neural activity are described herein. The neuromodulation device is an apparatus for the treatment of polycystic ovarian syndrome. In one aspect, the apparatus decreases the neural activity of a postganglionic ovary-innervating sympathetic nerve. Modulation in neural activity may be achieved using an apparatus comprising one or more stimulators each configured to apply a signal to a postganglionic ovary-innervating sympathetic nerve of the patient, a controller
(Continued)

Figure 1A:
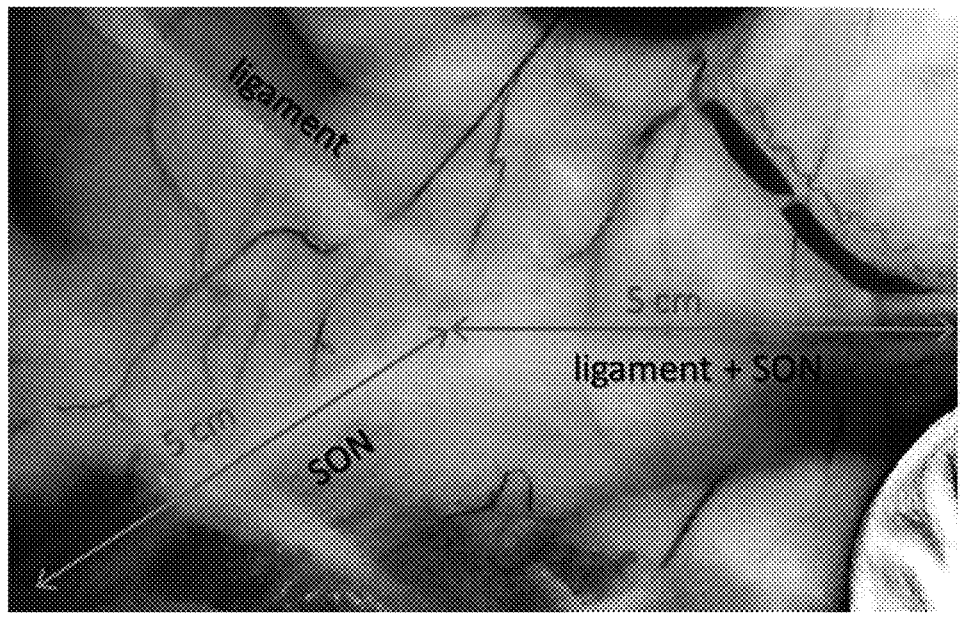

coupled to the one or more stimulators, the controller controlling the signal to be applied by each of the one or more stimulators, such that the signal decreases the neural activity of the nerve to produce a physiological and/or biochemical response in the patient, wherein the physiological and/or biochemical response comprises an improvement in one or more symptoms of polycystic ovarian syndrome.

1 Claim, 14 Drawing Sheets

(51) Int. Cl.
*A61N 1/05* (2006.01)
*A61N 1/20* (2006.01)
*A61N 5/06* (2006.01)
*A61N 7/00* (2006.01)

(52) U.S. Cl.
CPC ..... *A61N 1/36007* (2013.01); *A61N 1/36135* (2013.01); *A61N 5/0622* (2013.01); *A61N 7/00* (2013.01); A61F 2007/126 (2013.01); A61N 2005/063 (2013.01); A61N 2007/0026 (2013.01)

(56) References Cited

OTHER PUBLICATIONS

Written Opinion for International Application No. PCT/IB2016/050908.

\* cited by examiner

NEUROMODULATION DEVICE

This application is filed pursuant to 35 U.S.C. § 371 as a United States National Phase Application of International patent application Ser. No. PCT/IB2016/050908 filed Feb. 19, 2016 and claims priority to U.S. Patent Application Ser. No. 62/118,521 filed Feb. 20, 2015, and the entire contents of the foregoing applications are hereby incorporated by reference.

TECHNICAL FIELD

This invention relates to medical devices and, more particularly to medical devices that deliver neuromodulating therapy.

BACKGROUND

In mammals, ovulation is controlled by gonadotropins (luteinizing hormone and follicle-stimulating hormone) secreted by the pituitary and acting on the ovary. In addition to this hormonal control, the inventors have reported a role of neural control off ovulation (Lara H E, Dorfman M, Venegas M, Luza S M, Luna S L, Mayerhofer A, Guimaraes M A, Rosa ESAA, and Ramirez V D. Changes in sympathetic nerve activity of the mammalian ovary during a normal estrous cycle and in polycystic ovary syndrome: Studies on norepinephrine release. *Microsc Res Tech* 59: 495-502, 2002). Mammalian ovary receives a dense sympathetic innervation. These postganglionic sympathetic nerves originate from neuronal cell bodies of the ovarian ganglion and from cell bodies of the celiac and renal plexuses (Curry T E, Jr., Lawrence I E, Jr., Burden H W. Ovarian sympathectomy in the golden hamster: effects on estrous cyclicity and follicular development. *Exp Clin Endocrinol*. 1985; 86(3): 284-90, and Burden H W, Lawrence I E, Jr., Louis T M. The adrenergic innervation of the guinea pig ovary during prenatal and postnatal periods. *Acta Anat (Basel)*. 1985; 122(3): 193-6). The ovary receives its sympathetic innervation from two sources: (a) the ovarian plexus nerve (OPN), which is associated with the ovarian branch of the uterine artery (Neilson D., Seegar Jones, G., Woodruff, J D., Goldberg, B. The innervation of the ovary. *Obstetrical and Gynecological Survey*, 1970; 25(1): 889-904, and (b) the superior ovarian nerve (SON), which is at least partially associated with the ligament of ovary (also known as the suspensory ligament or the infundibulopelvic ligament) (Lawrence I E, Jr., Burden H W. The origin of the extrinsic adrenergic innervation to the rat ovary. *Anat Rec*. 1980; 196(1): 51-9; and Neilson, supra)).

In general, the superior ovarian nerve fibers innervate preponderantly the secretory components of the ovary, i.e., interstitial glands and follicles, whereas the ovarian plexus nerve fibers are mostly perivascular (Lawrence, supra). Although there is some variation in the way that sympathetic nerves reach the ovary, no differences have been found in the intraovarian distribution of sympathetic fibers, which is similar in all mammalian species (although the density of the network varies considerably among them (Jacobowitz D, Wallach E E. Histochemical and chemical studies of the autonomic innervation of the ovary. Endocrinology. 1967, 81(5):1132-9.)). Norepinephrine is the main neurotransmitter present in the ovary (Lara H E, McDonald J K, and Ojeda S R. Involvement of nerve growth factor in female sexual development. *Endocrinology*. 1990; 126(1): 364-75, Greiner M, Paredes A, Araya V, Lara H E. Role of stress and sympathetic innervation in the development of polycystic ovary syndrome. *Endocrine*. 2005; 28(3): 319-24, and Lara et al 2002, supra). The innervation of the gland has been shown to be involved in the regulation of ovary specific functions, such as steroidogenesis and early follicular development (Greiner et al, supra, and Lara et al, 2002, supra) by activating B-adrenergic receptors present in cells of the ovarian follicle.

Transection of the superior ovarian nerve, which carries the bulk of the sympathetic innervation to ovarian endocrine cells has been observed to restore estrous cyclicity and ovulation (Ovarian steroidal response to gonadotropins and beta-adrenergic stimulation is enhanced in polycystic ovary syndrome: role of sympathetic innervation; Barria A, Leyton V, Ojeda S R, Lara H E; Endocrinology. 1993 December; 133(6):2696-703). In contrast, a sustained increase in sympathetic activity by estradiol administration (1), chronic sympathetic stress (2), or pharmacological β-adrenergic receptor activation (3) causes the appearance of a polycystic phenotype in the rat ovary, which in many aspects resembles the polycystic ovary syndrome in women (1—Lara H E, Dissen G A, Leyton V, Paredes A, Fuenzalida H, Fiedler J L, and Ojeda S R. An increased intraovarian synthesis of nerve growth factor and its low affinity receptor is a principal component of steroid-induced polycystic ovary in the rat. *Endocrinology* 141: 1059-1072, 2000; 2—Dorfman M, Arancibia S, Fiedler J L, and Lara H E. Chronic intermittent cold stress activates ovarian sympathetic nerves and modifies ovarian follicular development in the rat. *Biol Reprod* 68: 2038-2043, 2003; and 3—Luna S L, Neuman S, Aguilera J, Brown D I, and Lara H E. In vivo β-adrenergic blockade by propranolol prevents isoproterenol-induced polycystic ovary in adult rats. *Horm Metab Res* 44: 676-681, 2012).

Polycystic ovary syndrome (PCOS) is often characterized by hyperandrogenism and a build-up of fluid-filled follicles (cysts), which do not undergo rupture during their normal maturation cycle. PCOS is the most prevalent ovarian pathology in women, affecting 5% to 12% of women of reproductive age, leading to endocrine/metabolic disorder. One of the principal symptoms of PCOS is anovulation, resulting in irregular menstruation and infertility. In addition, androgen secretion by the cysts in PCOS patients leads to masculinizing effects, such as acne and hirsutism. Recently, suppression of sympathetic activity by acupuncture was found to reduce the PCOS symptoms (Stener-Victorin E, Jedel E, and Manneras L. Acupuncture in polycystic ovary syndrome: current experimental and clinical evidence. *J Neuroendocrinol* 20: 290-298, 2008).

Current treatment of PCOS principally involves lifestyle changes such as weight loss and exercise, and as such PCOS presents a significant unmet medical need. Current treatment options focus on the symptoms, rather than the underlying cause, which is multi-factorial and not fully understood. For example, estrogen receptor modulators (e.g. clomiphene and metformin) and gonadatotrophins may be prescribed to induce regular cycling and ovulation, and laparoscopic ovarian drilling may be used to destroy the ovarian tissue that produces androgens. The fact that the pharmacological approach is principally focused to restore the function of reproductive hypothalamus, and the surgical procedure is focused at the ovary, means that the real cause could involve the complete organism and the brain-ovary connection.

WO2013/134548 proposes ovarian neuromodulation as a treatment for PCOS. More particularly, the inventors propose the destruction or ablation of the nerves adjacent to the ovarian blood vessel with a neuromodulation assembly which is intravascularly positioned within an ovarian blood vessel, although the examples section WO2013/134548 relate to a different intervention (renal neuromodulation) and show no indication of a positive treatment effect of this procedure (or indeed ovarian nerve ablation) on PCOS symptoms. However, this approach may also affect ovarian blood flow through the ovarian artery (Hotta, H. et al. *J. Physiol. Sci.* 2008 58(2): 133-138), modulating the exposure of the ovary to circulating hormones from the hypothalamus and pituitary.

SUMMARY OF INVENTION

Surprisingly, the present inventors have demonstrated that, in a recognized rat model of polycystic ovarian syndrome, by modulating the sympathetic neural signaling to the polycystic ovary by postganglionic sympathetic nerves, the formation of cysts is ameliorated. Additionally, normal estrous cycling is restored. A neuromodulation device that modulates the sympathetic neural activity in one or more of these nerves provides an effective treatment for polycystic ovarian syndrome.

Therefore, in accordance with a first aspect of the invention there is provided an apparatus for modulating the neural activity of a postganglionic ovary-innervating sympathetic nerve of a patient, the apparatus comprising: one or more neural interfacing elements (e.g., electrical or other stimulators) configured to apply a signal to the postganglionic ovary-innervating sympathetic nerve, optionally at least two such stimulators; and a controller coupled to the stimulator or stimulators in a wired or wireless fashion, the controller controlling the signal to be applied by the one or more stimulators, such that the signal modulates the neural activity of the nerve to produce a physiological response in the patient. The physiological response may be an improvement in one or more symptoms of polycystic ovarian syndrome, e.g., a change in the follicular maturation process in the ovary of the patient. The apparatus herein provided is favorably indicated for the treatment of polycystic ovarian syndrome, thus, the invention also provides an apparatus for the treatment of polycystic ovarian syndrome comprising: one or more stimulators configured to apply a signal to the postganglionic ovary-innervating sympathetic nerve, optionally at least two such stimulators; and a controller coupled to the stimulator or stimulators in a wired or wireless fashion, the controller controlling the signal to be applied by the one or more stimulators, such that the signal modulates the neural activity of the nerve to produce a physiological, e.g., therapeutic response in the patient. The physiological (e.g., therapeutic) response may be an improvement in one or more symptoms of polycystic ovarian syndrome in the patient.

In a second aspect, the invention provides a method of treating polycystic ovarian syndrome in a patient, the method comprising: implanting in the patient an apparatus according to the first aspect; positioning at least one stimulator of the apparatus in signaling contact with a postganglionic ovary-innervating sympathetic nerve of the patient; and activating the apparatus (for example, in a time-dependent and symptom-dependent manner). In certain embodiments, the patient has left and right postganglionic ovary-innervating sympathetic nerves, and the method comprises positioning at least one stimulator of the apparatus in signaling contact with both each of left and right postganglionic ovary-innervating sympathetic nerves. In certain embodiments, the postganglionic ovary-innervating sympathetic nerve is the superior ovarian nerve. In certain embodiments, the postganglionic ovary-innervating sympathetic nerve is the non-ligament-associated portion of the superior ovarian nerve.

In a third aspect, the invention provides a method of treating polycystic ovarian syndrome in a patient, the method comprising applying a signal to a postganglionic ovary-innervating sympathetic nerve of said patient to modulate the neural activity of said nerve in the patient. In certain embodiments, the signal is applied by a neuromodulation device or apparatus comprising one or more stimulators configured to apply the signal.

In a fourth aspect, the invention provides a neuromodulatory electrical waveform for use in treating polycystic ovarian syndrome in a patient, wherein the waveform is a kilohertz alternating current (AC) waveform having a frequency of 1 to 50 KHz, such that, when applied to a postganglionic ovary-innervating sympathetic nerve of the patient, the waveform inhibits neural signalling in the nerve or nerves to which the signal is applied.

In a fifth aspect, the invention provides use of a neuromodulation device or apparatus for the treatment of polycystic ovarian syndrome by modulating neural activity in a postganglionic ovary-innervating sympathetic nerve of the patient.

DETAILED DESCRIPTION

Figures

Figure 1B:
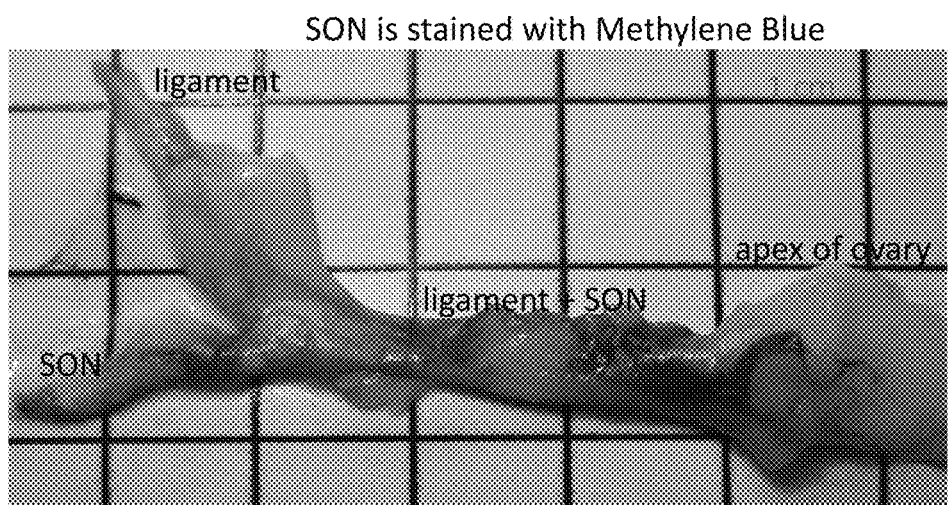
Figure 1C:
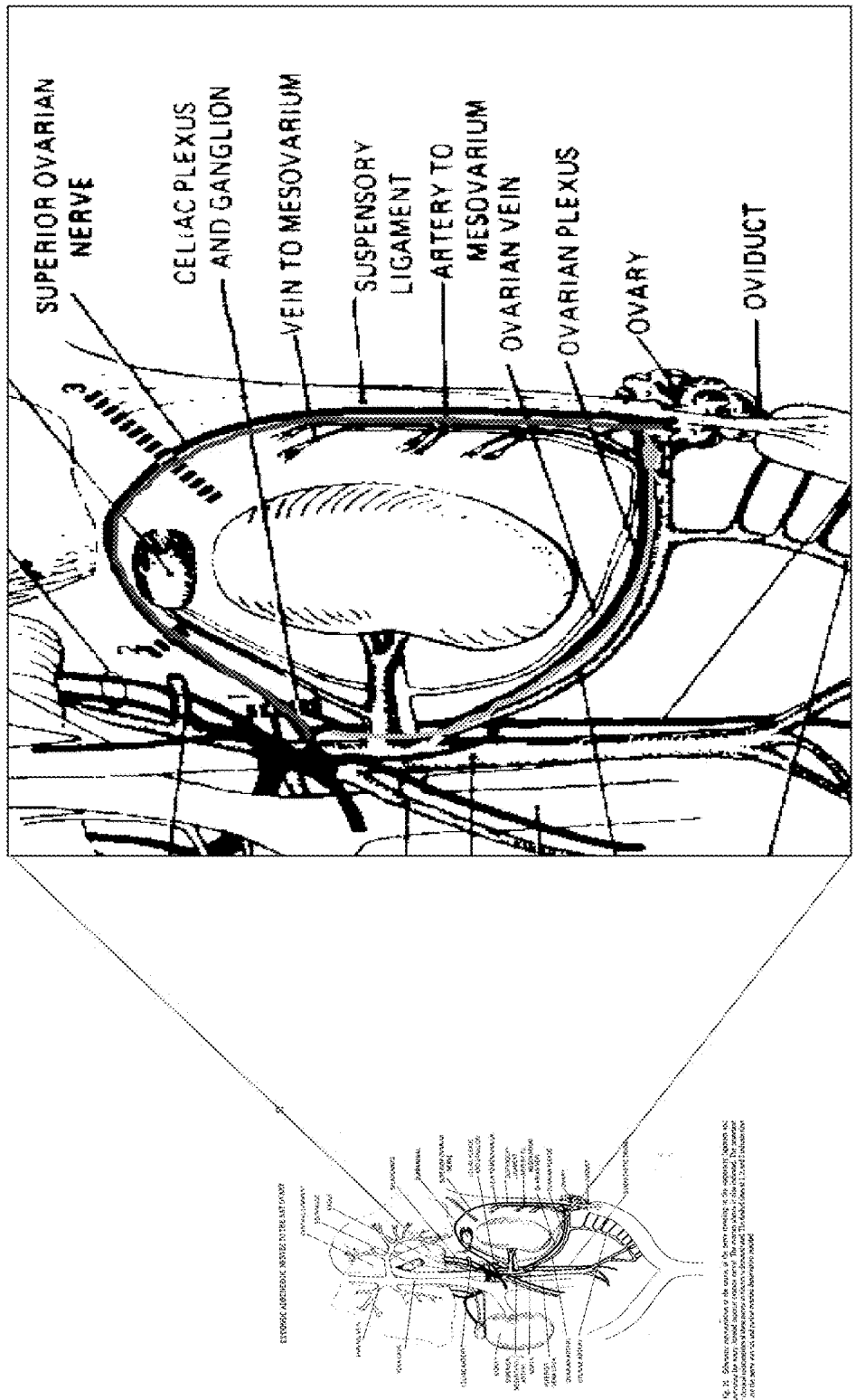

FIGS. 1A-C: FIG. 1 (A) Photograph of the innervation of the ovary in the dog before, and (B) after dissection. (C) Diagram showing the innervation of the ovary in the rat.

Figure 2A:
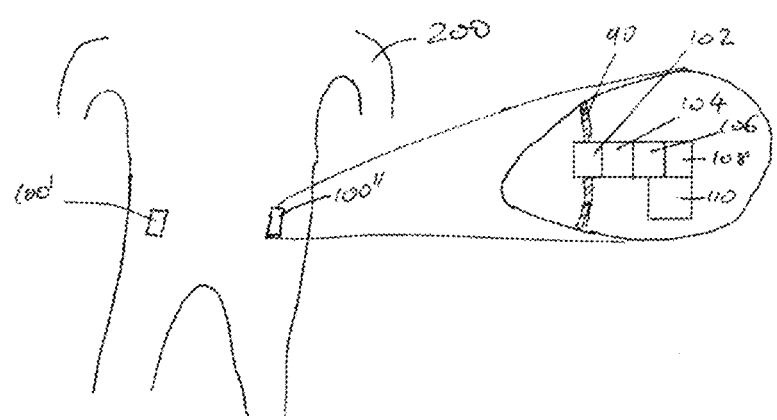
Figure 2B:
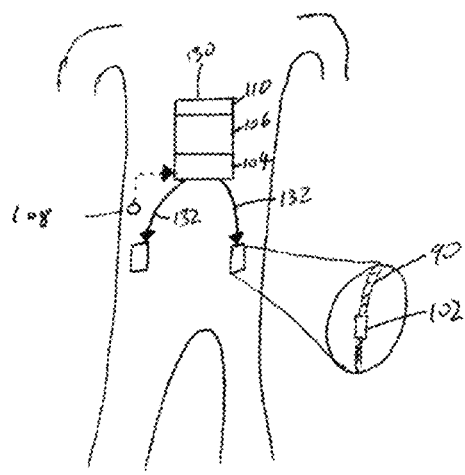
Figure 2C:
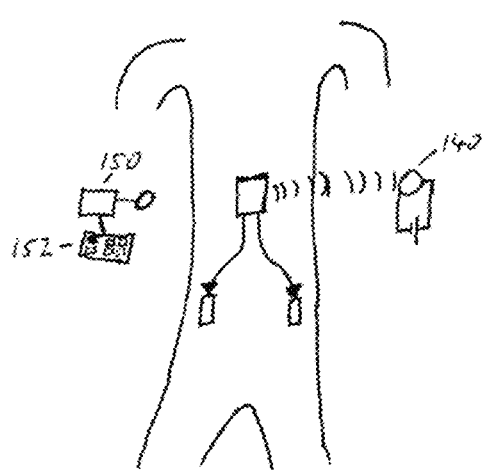

FIGS. 2A-C: Schematic drawings showing how apparatuses, devices and methods according to the invention can be put into effect.

Figure 3:
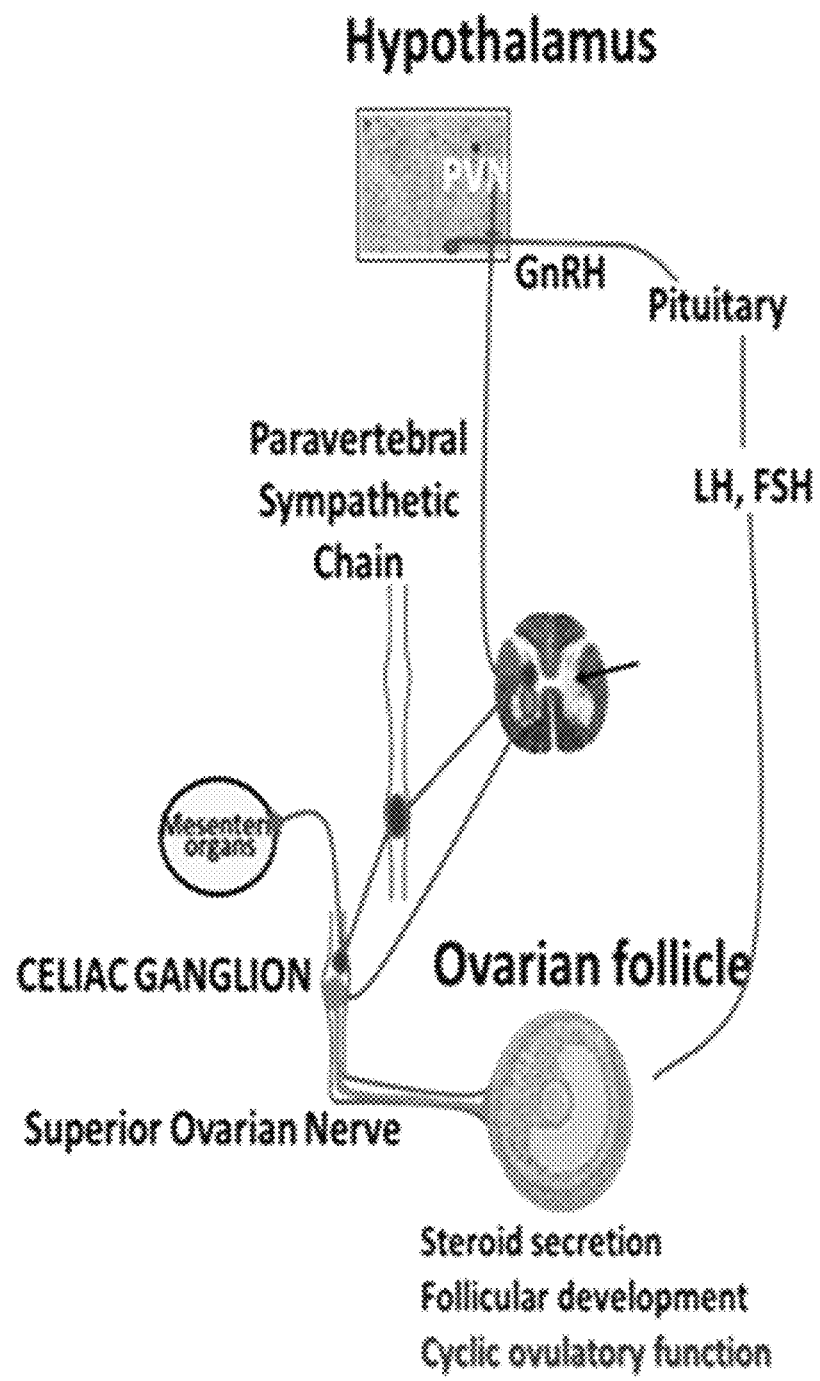

FIG. 3: Schematic drawing showing the interrelationship of neural and endocrine (hormonal) regulation of the ovarian cycle and ovulation.

Figure 4:
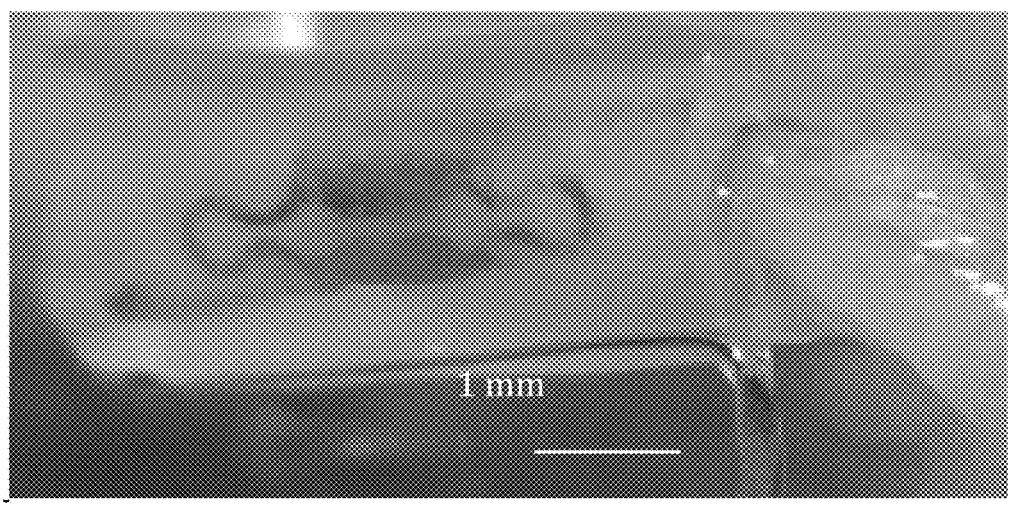

FIG. 4: Photograph showing a cuff electrode on the rat SON.

Figure 5:
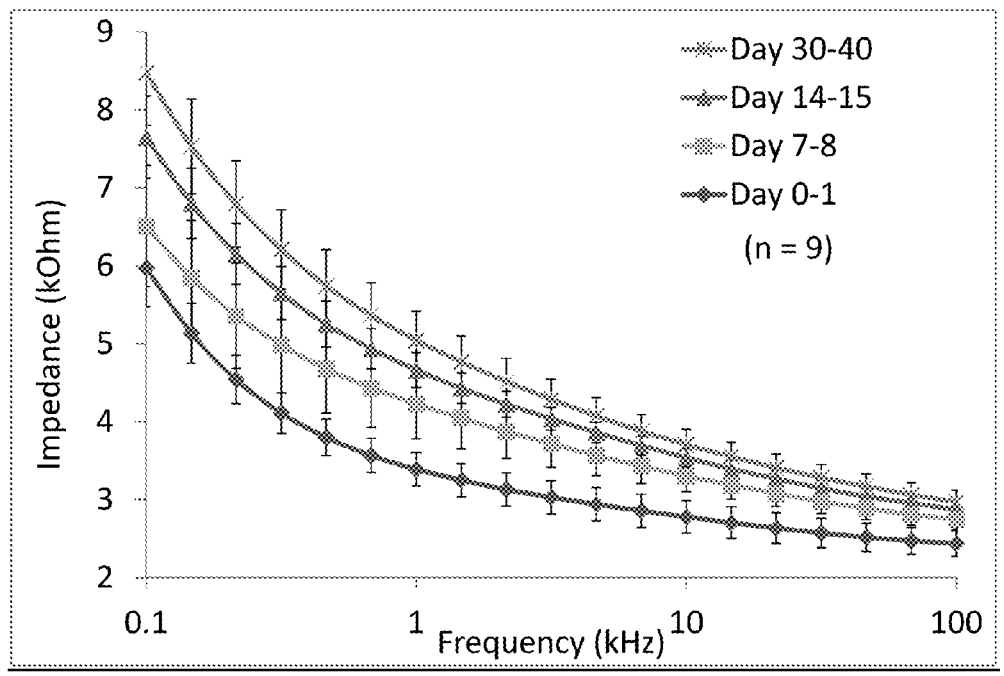

FIG. 5: Graph illustrating electrical impedance change over time recorded from a cuff electrode on the SON.

Figure 6:
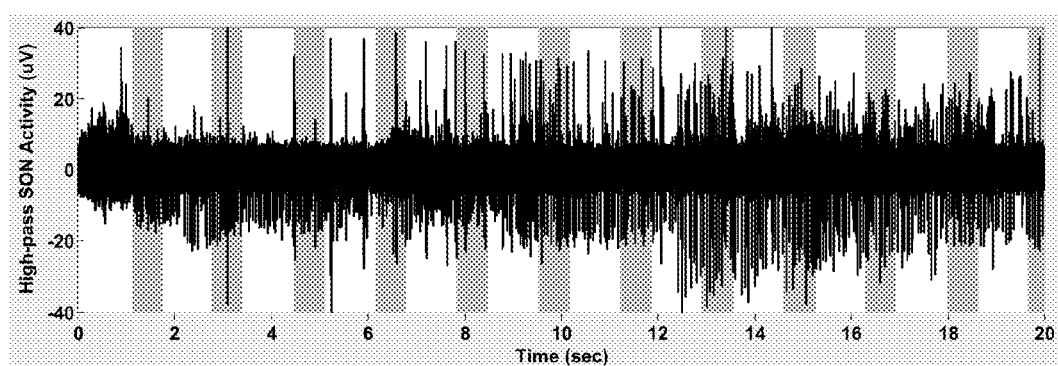

FIG. 6: Graph of electrical neural recording from a cuff electrode on the SON.

Figure 7A:
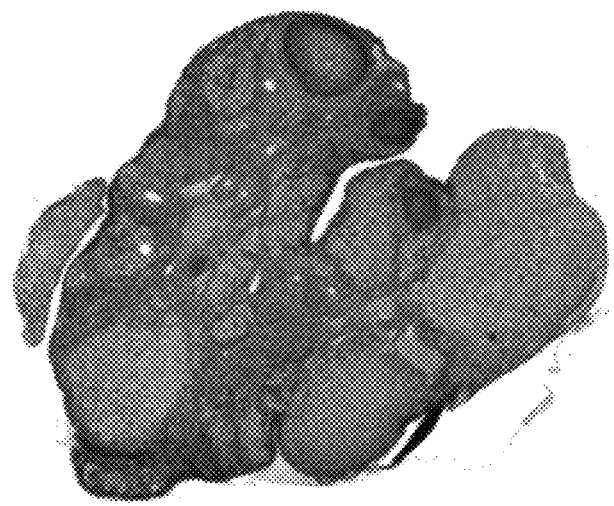
Figure 7B:
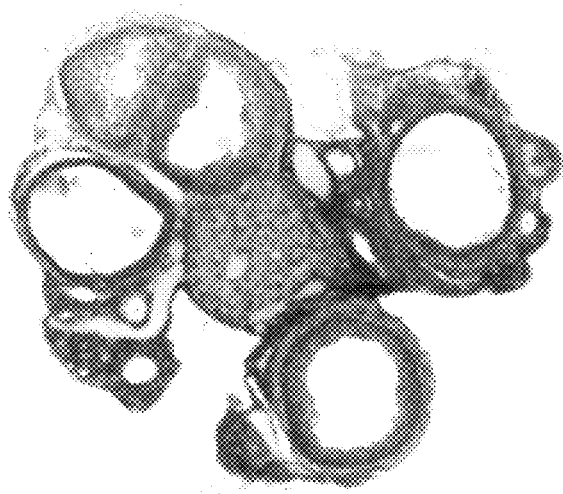

FIGS. 7A-B: Photographs illustrating representative ovarian phenotype: (A) normal follicles in intact rats, and (B) lack of normal follicles and abundance of cysts in the Estradiol Valerate (EV) model of polycystic ovarian syndrome.

Figure 8A:
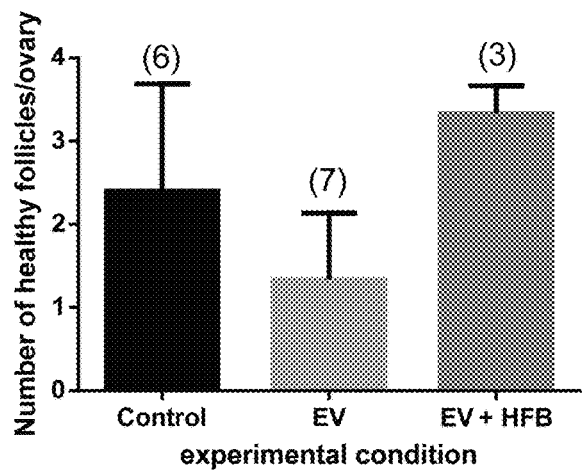
Figure 8B:
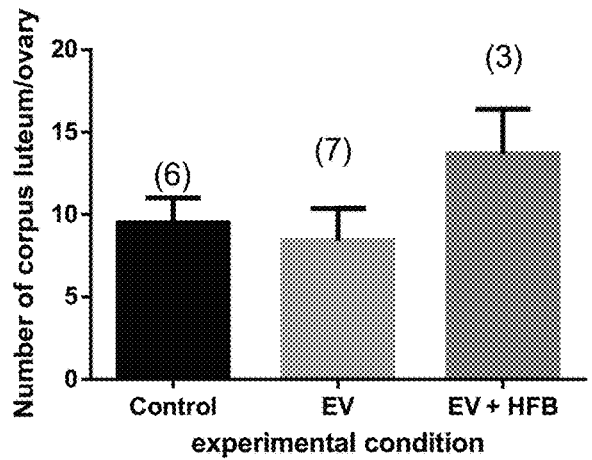
Figure 8C:
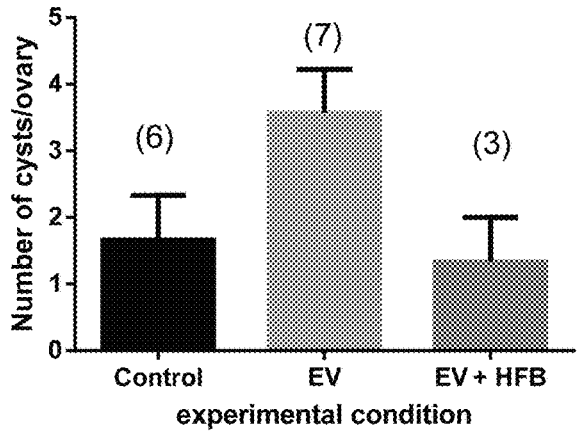

FIGS. 8A-C: Graphs illustrating effect of EV and high frequency (HF) block on ovarian morphological phenotype: (A) appearance of healthy follicles, (B) corpora lutea, and (C) cysts.

Figure 9:
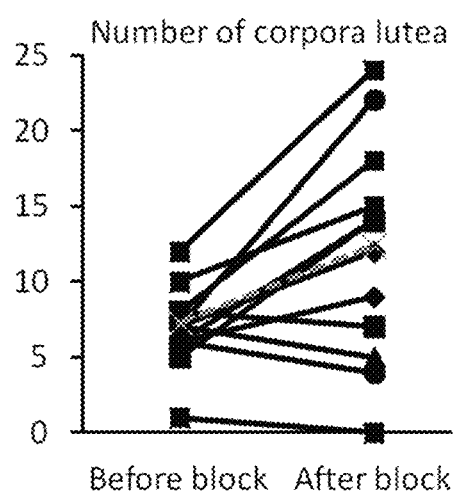

FIG. 9: Graph illustrating the effect of HF block on the number of corpora lutea in the EV-treated animals. Within-animal comparison of ovarian morphology was done using one ovary dissected before and another after the HF block.

Figure 10:
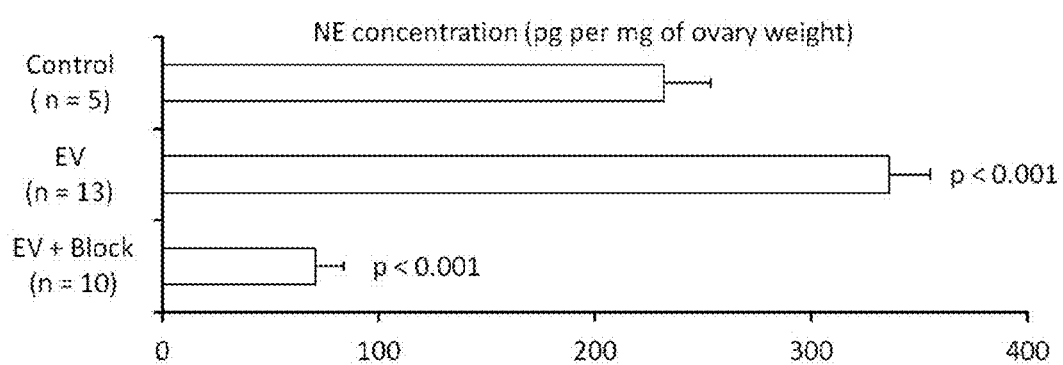

FIG. 10: Graph illustrating the effect of EV treatment and HF block on ovarian norephinephrine levels.

Figure 11:
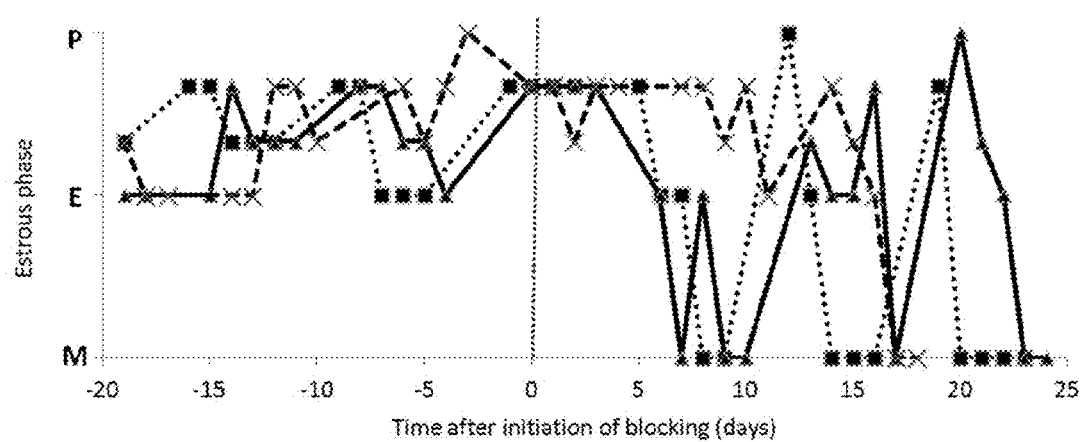

FIG. 11: Graph illustrating the effect of high-frequency (HF) block on the estrous cycling activity. P (proestrus), E (estrus) and D (diestrus), represent the different stages of the ovulatory cycle in the rat. Rat ovulates the night between P and E, it prepares for the next cycle during diestrus and return with a next ovulatory cycle. Rats stop cycling after one month of EV administration but recover ovulatory cycling activity after high frequency block (HFB). Horizontal bar indicates the duration of applied HFB.

Figure 12:
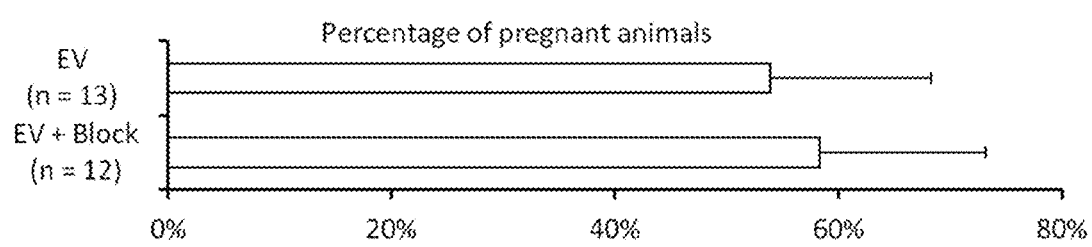

FIG. 12: Graph illustrating the effect of high-frequency (HF) block on the fertility of animals.

The terms as used herein are given their conventional definition in the art as understood by the skilled person, unless otherwise defined below. In the case of any inconsistency or doubt, the definition as provided herein should take precedence.

As used herein, application of a signal may equate to the transfer of energy in a suitable form to carry out the intended effect of the signal. That is, application of a signal to a nerve or nerves may equate to the transfer of energy to the nerve(s) to carry out the intended effect. For example, the energy transferred may be electrical, mechanical (including acoustic, such as ultrasound), electromagnetic (e.g. optical), magnetic or thermal energy. It is noted that application of a signal as used herein does not include a pharmaceutical intervention.

As used herein, a "non-destructive signal" is a signal as defined above that, when applied, does not irreversibly damage the underlying neural signal conduction ability. That is, application of a non-destructive signal maintains the ability of the nerve or nerves (or fibers thereof) to conduct action potentials when application of the signal ceases, even if that conduction is in practice inhibited or blocked as a result of application of the non-destructive signal.

As used herein, postganglionic ovary-innervating sympathetic nerve is taken to mean those sympathetic (e.g., efferent) nerves which innervate the ovary and are derived from the ovarian, celiac and renal plexuses. Examples of such nerves are the superior ovarian nerve and the ovarian plexus nerve. In a preferred embodiment the postganglionic ovary-innervating sympathetic nerve is the superior ovarian nerve.

As used herein, the superior ovarian nerve (SON) is taken to mean the sympathetic nerve that is at least partially associated with the ligament of ovary (also known as the suspensory ligament or the infundibulopelvic ligament). In dogs, approximately half-way through its course to the ovary, the SON merges with the ligament of ovary (FIG. 1A-B). Thus, there is at least a portion of the nerve which is not associated with the ligament of ovary—this region of the SON is referred to herein as the "non-ligament-associated SON".

As used herein, the ovarian plexus nerve (OPN) is taken to mean the sympathetic nerve from the celiac ganglion that innervates the ovary and runs inferior to the kidney (FIG. 1C).

As used herein, "neural activity" of a nerve is taken to mean the signaling activity of the nerve, for example the amplitude, frequency and/or pattern of action potentials in the nerve.

Modulation of neural activity, as used herein, is taken to mean that the signaling activity of the nerve is altered from the baseline neural activity—that is, the signaling activity of the nerve in the patient prior to any intervention. Such modulation may increase, inhibit, block, or otherwise change the neural activity compared to baseline activity.

Where the modulation of neural activity is an increase of neural activity, this may be an increase in the total signaling activity of the whole nerve, or that the total signaling activity of a subset of nerve fibers of the nerve is increased, compared to baseline neural activity in that part of the nerve.

Where the modulation of neural activity is inhibition of neural activity, such inhibition may be partial inhibition. Partial inhibition may be such that the total signaling activity of the whole nerve is partially reduced, or that the total signaling activity of a subset of nerve fibers of the nerve is fully reduced (i.e. there is no neural activity in that subset of fibers of the nerve), or that the total signaling of a subset of nerve fibers of the nerve is partially reduced compared to baseline neural activity in that subset of fibers of the nerve. Where the modulation of neural activity is inhibition of neural activity, this also encompasses full inhibition of neural activity in the nerve—that is, there is no neural activity in the whole nerve.

Where modulation of neural activity is a block on neural activity, such blocking may be a partial block—i.e. blocking of neural activity in a subset of nerve fibers of the nerve. Alternatively, such blocking may be a full block—i.e. blocking of neural activity in the whole nerve. A block on neural activity is understood to be blocking neural activity from continuing past the point of the block. That is, when the block is applied, action potentials may travel along the nerve or subset of nerve fibers to the point of the block, but not beyond the block.

Modulation of neural activity may also be an alteration in the pattern of action potentials. It will be appreciated that the pattern of action potentials can be modulated without necessarily changing the overall frequency or amplitude. For example, modulation of the neural activity may be such that the pattern of action potentials is altered to more closely resemble a healthy state rather than a disease state—i.e. to more closely resemble the pattern in a fertile individual.

Modulation of neural activity may comprise altering the neural activity in various other ways, for example increasing or inhibiting a particular part of the neural activity and/or stimulating new elements of activity, for example in particular intervals of time, in particular frequency bands, according to particular patterns and so forth. Such altering of neural activity may for example represent both increases and/or decreases with respect to the baseline activity.

Modulation of the neural activity may be temporary. As used herein, "temporary" is taken to mean that the modulated neural activity (whether that is an increase, inhibition, block or other modulation of neural activity or change in pattern versus baseline activity) is not permanent. That is, the neural activity following cessation of the signal is substantially the same as the neural activity prior to the signal being applied—i.e. prior to modulation.

Modulation of the neural activity may be persistent. As used herein, "persistent" is taken to mean that the modulated neural activity (whether that is an increase, inhibition, block or other modulation of neural activity or change in pattern versus baseline activity) has a prolonged effect. That is, upon cessation of the signal, neural activity in the nerve remains substantially the same as when the signal was being applied—i.e. the neural activity during and following modulation is substantially the same.

Modulation of the neural activity may be corrective. As used herein, "corrective" is taken to mean that the modulated neural activity (whether that is an increase, inhibition, block or other modulation of neural activity or change in pattern versus baseline activity) alters the neural activity towards the pattern of neural activity in a healthy individual. That is, upon cessation of the signal, neural activity in the nerve more closely resembles the pattern of action potentials in the nerve observed in a fertile subject than prior to modulation, preferably substantially fully resembles the pattern of action potentials in the nerve observed in a fertile subject.

Such corrective modulation caused by the signal can be any modulation as defined herein. For example, application of the signal may result in a block on neural activity, and upon cessation of the signal, the pattern of action potentials in the nerve resembles the pattern of action potentials observed in a fertile subject. By way of further example, application of the signal may result modulation such that the neural activity resembles the pattern of action potentials observed in a fertile subject, and upon cessation of the signal, the pattern of action potentials in the nerve resembles the pattern of action potentials observed in a fertile individual.

Polycystic ovarian (or ovary) syndrome (PCOS), also known as hyperandrogenic anovulation (HA) or Stein-Leventhal syndrome is a female endocrine disorder. Although often characterized by a build-up of medium-size fluid-filled follicles (cysts) which do not undergo rupture during their normal maturation cycle. Because of the difficult to discriminate polycystic ovary from the ovarian cystic condition normally found during hyperandrogenism of adrenal origin, the Rotterdam criteria (Human Reproduction; *Revised* 2003 *consensus on diagnostic criteria and long-term health risks related to polycystic ovary syndrome (PCOS)* 19(1) 41-7, 2004), define PCOS when the patient presents 2 out of 3 of (i) polycystic ovaries, (ii) oligovulation or anovulation, and (iii) excess androgen activity.

As used herein, an "improvement in a measurable physiological and/or biochemical parameter" is taken to mean that for any given physiological and/or biochemical parameter, an improvement is a change in the value of that parameter in the patient towards the normal value or normal range for that value—i.e. towards the expected value in a fertile individual.

For an example, in a patient suffering from PCOS an improvement in a measurable parameter may be: a reduction in sympathetic tone; a reduction in the number of cysts in an ovary (e.g. by gynaecological ultrasound); an increase in proportion of ovulatory menstrual cycles; a change in the concentration or release pattern of an androgen, for example, a reduction in the concentration or release pattern of testosterone; or a change in the concentration or release pattern of one or more gonadotrophin, for example follicle stimulating hormone (FSH), luteinising hormone (LH), or chorionic gonadotrophin (CG), progesterone, and estrogen such that the concentration or release pattern more closely resembles that of a healthy female individual, assuming the patient is exhibiting abnormal values for the respective parameter.

As used herein, a physiological and/or biochemical parameter is not affected by modulation of the neural activity if the parameter does not change as a result of the modulation from the average value of that parameter exhibited by the subject or patient when no intervention has been performed—i.e. it does not depart from the baseline value for that parameter.

The skilled person will appreciate that the baseline for any neural activity or physiological and/or biochemical parameter in an individual need not be a fixed or specific value, but rather can fluctuate within a normal range or may be an average value with associated error and confidence intervals. Suitable methods for determining baseline values would be well known to the skilled person.

As used herein, a measurable physiological and/or biochemical parameter is detected in a patient when the value for that parameter exhibited by the patient at the time of detection is determined. A detector is any element able to make such a determination.

A "predefined threshold value" for a physiological and/or biochemical parameter is the value for that parameter where that value or beyond must be exhibited by a subject or patient before the intervention is applied. For any given parameter, the threshold value may be defined as a value indicative of a polycystic ovarian state or a particular physiological and/or biochemical state (e.g. the patient being in a particular phase of the ovarian cycle). Examples of such predefined threshold values include sympathetic tone (neural, hemodynamic (e.g. heart rate, blood pressure, heart rate variability) or circulating plasma/urine biomarkers) greater than a threshold sympathetic tone, or greater than a sympathetic tone in a fertile individual; ovarian nor-epinephrine concentration, plasma nor-epinephrine concentration; plasma androgen concentration; plasma androgen concentration; plasma testosterone concentration; plasma gonadotrophin concentration, plasma FSH concentration, plasma LH concentration, plasma thyroid hormone concentration, glucose tolerance and/or insulin sensitivity (both measurable by, for example, the homeostasis model assessment), and/or plasma progesterone concentration greater or less than in a healthy, non-PCOS, fertile female individual, or greater or less than a threshold value. Appropriate values for any given parameter would be simply determined by the skilled person.

Such a threshold value for a given physiological and/or biochemical parameter is exceeded if the value exhibited by the patient is beyond the threshold value—that is, the exhibited value is a greater departure from the normal or healthy value for that parameter than the predefined threshold value.

Treatment of PCOS is characterized by an improvement in one or more of the symptoms of PCOS in the patient. That is, as a result of treatment, the patient exhibits one or more of: a reduction in sympathetic tone; a reduction in the appearance of polycystic ovaries (e.g. by gynecological ultrasound); an increase in proportion of ovulatory menstrual cycles; a change in the concentration or release pattern of an androgen, for example, a reduction in androgen activity, for example a reduction in the concentration or release pattern of testosterone; or a change in the concentration or release pattern of one or more gonadotrophin, for example follicle stimulating hormone (FSH), luteinizing hormone (LH), or chorionic gonadotrophin (CG), progesterone, and estrogen such that the concentration or release pattern more closely resembles that of a healthy female individual, assuming the patient is exhibiting abnormal values for the respective parameter. Such symptoms, and improvements therein, are readily determined by the skilled person.

Treatment of PCOS may be prophylactic or therapeutic. There is evidence to suggest that a high stress condition is one factor underlying the development of PCOS, and thus it may be desirable to control sympathetic tone in patients with such a condition, to provide for adequate and appropriate androgen production and follicular development.

A "neuromodulation device" as used herein is a device configured to modulate the neural activity of a nerve. Neuromodulation devices as described herein comprise at least one neural interfacing element (e.g. a stimulus-generating device or electrical or other stimulatoror transducer: these terms may be used interchangeably to refer to an element of an apparatus that is capable of delivering a signal that modulates electrical activity, e.g., action potentials, in a nerve) that is capable of effectively applying a signal to a nerve. In those embodiments in which the neuromodulation device is at least partially implanted in the patient, the elements of the device that are to be implanted in the patient are constructed such that they are suitable for such implantation. Such suitable constructions would be well known to the skilled person. Indeed, various fully implantable neuromodulation devices are currently available, such as the vagus nerve stimulator of SetPoint Medical, in clinical development for the treatment of rheumatoid arthritis (*Ar-*

*thritis & Rheumatism*, Volume 64, No. 10 (Supplement), page S195 (Abstract No. 451), October 2012. *"Pilot Study of Stimulation of the Cholinergic Anti-Inflammatory Pathway with an Implantable Vagus Nerve Stimulation Device in Patients with Rheumatoid Arthritis"*, Frieda A. Koopman et al), and the INTERSTIM™ device (Medtronic, Inc), a fully implantable device utilized for sacral nerve modulation in the treatment of overactive bladder.

As used herein, "implanted" is taken to mean positioned within the patient's body. Partial implantation means that only part of the device is implanted—i.e. only part of the device is positioned within the patient's body, with other elements of the device external to the patient's body. "Wholly implanted" means that the entire of the device is positioned within the patient's body.

As used herein, "charge-balanced" in relation to a DC current is taken to mean that the positive or negative charge introduced into any system (e.g. a nerve) as a result of a DC current being applied is balanced by the introduction of the opposite charge in order to achieve overall (i.e. net) neutrality.

A neuromodulation device that modulates the sympathetic neural activity in these nerves will provide an effective treatment for PCOS. Accordingly, such a device is an apparatus for the treatment of polycystic ovarian syndrome in a patient.

In one aspect of the invention there is provided an apparatus for modulating the neural activity of a postganglionic ovary-innervating sympathetic nerve of a patient, the apparatus comprising: one or more neural interfacing elements (e.g. electrical or other stimulators or transducers) configured to apply a signal to the nerve, optionally at least two such stimulators; and a controller coupled to the stimulator or stimulators, the controller controlling the signal to be applied by the one or more stimulators, such that the signal modulates the neural activity of the nerve to produce a physiological and/or biochemical response in the patient. The physiological and/or biochemical response may be an improvement in one or more symptoms of polycystic ovarian syndrome in the patient.

In certain embodiments, the signal applied by the one or more stimulators is a non-destructive signal.

In certain such embodiments, the signal applied by the one or more stimulators is an electrical signal, an optical signal, an ultrasonic signal, or a thermal signal. In those embodiments in which the apparatus has at least two stimulators, the signal which each of the stimulators is configured to apply is independently selected from an electrical signal, an optical signal, an ultrasonic signal, and a thermal signal. That is, each stimulator may be configured to apply a different signal. Alternatively, in certain embodiments each stimulator is configured to apply the same signal.

In certain embodiments, each of the one or more stimulators may be comprised of one or more electrodes, one or more photon sources, one or more ultrasound stimulators, one more sources of heat, or one or more other types of stimulator arranged to put the signal into effect.

In certain embodiments, the signal or signals applied by the one or more stimulators is an electrical signal, for example a voltage or current. In certain such embodiments the signal applied comprises a direct current (DC) waveform, such as a charge-balanced DC waveform, or an alternating current (AC) waveform, or both a DC and an AC waveform. In certain embodiments, the signal comprises an AC waveform of kilohertz frequency. In certain embodiments, the signal comprises a DC ramp followed by a plateau and charge-balancing, followed by a first AC waveform, wherein the amplitude of the first AC waveform increases during the period in which the first AC waveform is applied, followed by a second AC waveform having a lower amplitude and/or lower frequency than the first AC waveform. In certain such embodiments, the DC ramp, first AC waveform and second AC waveform are applied substantially sequentially.

In those embodiments in which the signal applied by the one or more stimulators is an electrical signal, at least one of the one or more stimulators is an electrode configured to apply the electrical signal. In certain such embodiments, all the stimulators are electrodes configured to apply an electrical signal, optionally the same electrical signal.

In certain embodiments in which the signal applied by the one or more stimulators comprises one or more AC waveforms, at least one of the AC waveforms has a frequency of 1 to 50 kHz, optionally 5 to 50 KHz, optionally 5-20 KHz, such as between 5-10 KHz or between 10-20 KHz.

In certain embodiments the applied AC waveform is biphasic and shaped either as a rectangular or sine wave. In certain embodiments, the applied AC waveform is either voltage-controlled or current-controlled.

In certain embodiments wherein the signal applied by the one or more stimulators is a thermal signal, the signal reduces the temperature of the nerve (i.e. cools the nerve). In certain alternative embodiments, the signal increases the temperature of the nerve (i.e. heats the nerve). In certain embodiments, the signal both heats and cools the nerve.

In those embodiments in which the signal applied by the one or more stimulators is a thermal signal, at least one of the one or more stimulators is a stimulator configured to apply a thermal signal. In certain such embodiments, all the stimulators are configured to apply a thermal signal, optionally the same thermal signal.

In certain embodiments, one or more of the one or more stimulators comprise a Peltier element configured to apply a thermal signal, optionally all of the one or more stimulators comprise a Peltier element. In certain embodiments, one or more of the one or more stimulators comprise a laser diode configured to apply a thermal signal, optionally all of the one or more stimulators comprise a laser diode configured to apply a thermal signal. In certain embodiments, one or more of the one or more stimulators comprise a electrically resistive element configured to apply a thermal signal, optionally all of the one or more stimulators comprise a electrically resistive element configured to apply a thermal signal.

In certain alternative embodiments, the signal applied by the one or more stimulators is not a thermal signal.

In certain embodiments the signal applied by the one or more stimulators is a mechanical signal, optionally an ultrasonic signal. In certain alternative embodiments, the mechanical signal applied by the one or more stimulators is a pressure signal.

In certain embodiments the signal applied by the one or more stimulators is an electromagnetic signal, optionally an optical signal. In certain such embodiments, the one or more stimulators comprise a laser and/or a light emitting diode configured to apply the optical signal.

In certain embodiments, the physiological and/or biochemical response produced in the patient is one or more of: a reduction in sympathetic tone; a reduction in the appearance of polycystic ovaries (e.g. by gynaecological ultrasound); an increase in proportion of ovulatory menstrual cycles; a change in the concentration or release pattern of an androgen, for example, a reduction in androgen activity, for example a reduction in the concentration or release pattern of testosterone; or a change in the concentration or release pattern of one or more gonadotrophin, for example follicle stimulating hormone (FSH), luteinising hormone (LH), or chorionic gonadotrophin (CG), progesterone, and oestrogen such that the concentration or release pattern more closely resembles that of a healthy female individual, assuming the patient is exhibiting abnormal values for the respective parameter.

In certain embodiments, the apparatus further comprises a detector element to detect one or more physiological and/or biochemical parameters in the patient. Such a detector element may be configured to detect the one or more physiological and/or biochemical parameters. That is, in such embodiments each detector may detect more than one physiological and/or biochemical parameter, for example all the detected physiological and/or biochemical parameters. Alternatively, in such embodiments each of the one or more detector elements is configured to detect a separate parameter of the one or more physiological and/or biochemical parameters detected.

In such certain embodiments, the controller is coupled to the detector element configured to detect one or more physiological and/or biochemical parameters, and causes the stimulator or stimulators to apply the signal when the physiological and/or biochemical parameter is detected to be meeting or exceeding a predefined threshold value.

In certain embodiments, the one or more detected physiological and/or biochemical parameters are selected from: sympathetic tone (neural, hemodynamic (e.g. heart rate, blood pressure, heart rate variability) or circulating plasma/urine biomarkers), ovarian nor-epinephrine concentration, plasma nor-epinephrine concentration, ovarian androgen concentration, plasma androgen concentration, ovarian testosterone concentration, plasma testosterone concentration, ovarian gonadotrophins concentration, plasma gonadotrophin concentration, ovarian FSH concentration, plasma FSH concentration, ovarian LH concentration, plasma LH concentration, ovarian oestrogen concentration, plasma oestrogen concentration, ovarian chorionic gonadotrophin concentration, plasma chorionic gonadotrophin concentration, ovarian progesterone concentration, plasma progesterone concentration, ovarian thyroid hormone concentration, plasma thyroid hormone concentration, plasma glucose concentration, insulin sensitivity.

A "predefined threshold value" for a physiological and/or biochemical parameter is the value for that parameter where that value or beyond must be exhibited by a subject or patient before the intervention is applied. For any given parameter, the threshold value may be defined as a value indicative of a polycystic ovarian state or a particular physiological and/or biochemical state (e.g. the patient being in a particular phase of the ovarian cycle). Examples of such predefined threshold values include sympathetic tone (neural, hemodynamic (e.g. heart rate, blood pressure, heart rate variability) or circulating plasma/urine biomarkers) greater than a threshold sympathetic tone, or greater than a sympathetic tone in a healthy non-PCOS fertile female individual; ovarian nor-epinephrine concentration, plasma nor-epinephrine concentration; plasma androgen concentration; plasma testosterone concentration; plasma gonadotrophin concentration, plasma FSH concentration, plasma LH concentration, plasma thyroid hormone concentration, glucose tolerance and/or insulin sensitivity (both measurable by, for example, the homeostasis model assessment), and/or plasma progesterone concentration greater or less than in a healthy, non-PCOS, fertile female individual, or greater or less than a threshold value. Appropriate values for any given parameter would be simply determined by the skilled person. In certain embodiments, the predefined threshold value is a plasma androgen concentration greater than in a healthy, non-PCOS, fertile female individual.

In certain embodiments, the one or more detected physiological parameters comprise an action potential or pattern of action potentials in a nerve of the patient, wherein the action potential or pattern of action potentials is associated with PCOS. In certain such embodiments, the nerve is a postganglionic ovary-innervating sympathetic nerve. In certain such embodiments, the nerve is a SON or an OPN. In a preferred embodiment, the nerve is a SON. In this embodiment, the detected pattern of action potentials may be associated with PCOS.

It will be appreciated that any two or more of the indicated physiological and/or biochemical parameters may be detected in parallel or consecutively. For example, in certain embodiments, the controller is coupled to a detector or detectors configured to detect the pattern of action potentials in the SON at the same time as the level of plasma androgens in the patient.

In certain embodiments, the postganglionic ovary-innervating sympathetic nerve to which the signal is applied is a superior ovarian nerve (SON), optionally the signal is also applied an ovarian plexus nerve.

In certain embodiments the modulation in neural activity as a result of applying the signal is inhibition of neural activity in the nerve or nerves. That is, in such embodiments, application of the signal results in the neural activity in at least part of the nerve(s) being reduced compared to the baseline neural activity in that part of the nerve. Such a reduction in activity could equally be across the whole nerve, in which case neural activity would be reduced across the whole nerve. Therefore, in certain such embodiments, a result of applying the signal is at least partial inhibition of neural activity in the nerve or nerves. In certain embodiments, a result of applying the signal is full inhibition of neural activity in the nerve or nerves.

In certain embodiments, the modulation in neural activity as a result of applying the signal is a block on neural activity in the nerve or nerves. That is, in such embodiments, the application of the signal blocks action potentials from travelling beyond the point of the block in at least a part of the nerve or nerves. In certain such embodiments, the modulation is a partial block. In certain alternative embodiments, the modulation is a full block.

In certain embodiments, the modulation in neural activity as a result of applying the signal is an increase in neural activity in the nerve or nerves. That is, in such embodiments, application of the signal results in the neural activity in at least part of the nerve or nerves being increased compared to the baseline neural activity in that part of the nerve. Such an increase in activity could equally be across the whole nerve, in which case neural activity would be increased across the whole nerve or nerves. Therefore, in certain such embodiments, a result of applying the signal is an increase in neural activity in the nerve or nerves. In certain embodiments, a result of applying the signal is an increase in neural activity across the whole nerve or nerves.

In certain embodiments, the modulation in neural activity as a result of applying the signal is an alteration to the pattern of action potentials in the nerve or nerves. In certain such embodiments, the neural activity is modulated such that the resultant pattern of action potentials in the nerve or nerves resembles the pattern of action potentials in the nerve or nerves observed in a subject without PCOS.

Modulation of neural activity may comprise altering the neural activity in various other ways, for example increasing or inhibiting a particular part of the activity and stimulating new elements of activity, for example in particular intervals of time, in particular frequency bands, according to particular patterns and so forth. Such altering of neural activity may for example represent both increases and/or decreases with respect to the baseline activity.

In certain embodiments, the controller causes the signal to be applied intermittently. In certain such embodiments, the controller causes the signal to applied for a first time period, then stopped for a second time period, then reapplied for a third time period, then stopped for a fourth time period. In such an embodiment, the first, second, third and fourth periods run sequentially and consecutively. The series of first, second, third and fourth periods amounts to one application cycle. In certain such embodiments, multiple application cycles can run consecutively such that the signal is applied in phases, between which phases no signal is applied.

In such embodiments, the duration of the first, second, third and fourth time periods is independently selected. That is, the duration of each time period may be the same or different to any of the other time periods. In certain such embodiments, the duration of each of the first, second, third and fourth time periods is any time from 5 seconds (5 s) to 24 hours (24 h), 30 s to 12 h, 1 min to 12 h, 5 min to 8 h, 5 min to 6 h, 10 min to 6 h, 10 min to 4 h, 30 min to 4 h, 1 h to 4 h. In certain embodiments, the duration of each of the first, second, third and fourth time periods is 5 s, 10 s, 30 s, 60 s, 2 min, 5 min, 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h.

In certain embodiments wherein the controller causes the signal to be applied intermittently, the signal is applied for a specific amount of time per day. In certain such embodiments, the signal is applied for 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain such embodiments, the signal is applied continuously for the specified amount of time. In certain alternative such embodiments, the signal may be applied discontinuously across the day, provided the total time of application amounts to the specified time.

In certain embodiments wherein the controller causes the signal to be applied intermittently, the signal is applied only when the patient is in a specific physiological state. In certain such embodiments, the signal is applied only when the patient is in a specific phase of the ovarian cycle. In certain such embodiments, the signal is applied only when the patient is in the follicular phase. Alternatively, the signal is applied only when the patient is in the luteal phase or a subset of the follicular and/or luteal phase. In certain such embodiments, the apparatus further comprises a communication, or input, element via which the status of the patient (e.g. that they are in a particular stage of the ovarian cycle) can be indicated by the patient or a physician. In alternative embodiments, the apparatus further comprises a detector configured to detect the status of the patient, wherein the signal is applied only when the detector detects that the patient is in the specific state.

In certain alternative embodiments, the controller causes the signal to be permanently (e.g., continuously) applied for a prolonged period of time. That is, once begun, the signal is continuously applied to the nerve or nerves. It will be appreciated that in embodiments wherein the signal is a series of pulses, gaps between pulses do not mean the signal is not continuously applied. For example, the signal can be applied persistently to modulate neural activity for multiple estrous cycles to improve the therapeutic effect and restore physiological and/or biochemical function of the ovary (or ovaries). The signal can be applied persistently for at least 2, at least 3, at least or greater than 4 estrous cycles, at least or greater than 5 estrous cycles, or for at least or greater than 6 estrous cycles.

In certain embodiments of the apparatus, the modulation in neural activity caused by the application of the signal (whether that is an increase, inhibition, block or other modulation of neural activity) is temporary. That is, upon cessation of the signal, neural activity in the nerve or nerves returns substantially towards baseline neural activity within 1-60 seconds, or within 1-60 minutes, or within 1-24 hours, optionally 1-12 hours, optionally 1-6 hours, optionally 1-4 hours, optionally 1-2 hours. In certain such embodiments, the neural activity returns substantially fully to baseline neural activity. That is, the neural activity following cessation of the signal is substantially the same as the neural activity prior to the signal being applied—i.e. prior to modulation.

In certain alternative embodiments, the modulation in neural activity caused by the application of the signal or signals is substantially persistent. That is, upon cessation of the signal, neural activity in the nerve or nerves remains substantially the same as when the signal was being applied—i.e. the neural activity during and following modulation is substantially the same.

In certain embodiments, the modulation in neural activity caused by the application of the signal is partially corrective, preferably substantially corrective. That is, upon cessation of the signal, neural activity in the nerve or nerves more closely resembles the pattern of action potentials in the nerve(s) observed in a healthy subject than prior to modulation, preferably substantially fully resembles the pattern of action potentials in the nerve(s) observed in a subject without PCOS. In such embodiments, the modulation caused by the signal can be any modulation as defined herein. For example, application of the signal may result in a block on neural activity, and upon cessation of the signal, the pattern of action potentials in the nerve or nerves resembles the pattern of action potentials observed in an individual without PCOS. By way of further example, application of the signal may result in modulation such that the neural activity resembles the pattern of action potentials observed in a subject without PCOS, and upon cessation of the signal, the pattern of action potentials in the nerve or nerves resembles the pattern of action potentials observed in a subject without PCOS. It is hypothesized that such a corrective effect is the result of a positive feedback loop—that is, the underlying PCOS state is treated as result of the device and use in the claimed methods.

In certain embodiments, the apparatus is suitable for at least partial implantation into the patient. In certain such embodiments, the apparatus is suitable to be fully implanted in the patient.

In certain embodiments, the apparatus further comprises one or more power supply elements, for example a battery, and/or one or more communication elements. The battery may be a primary cell battery, a rechargeable battery that is recharged by inductive coupling. In one embodiment, the apparatus may be powered by direct inductive powering.

In a second aspect, the invention provides a method for treating polycystic ovarian syndrome in a patient, the method comprising implanting an apparatus according to the first aspect, positioning at least one stimulator of the apparatus in signaling contact with a postganglionic ovary-innervating sympathetic nerve of the patient, and activating the apparatus. In such embodiments, the stimulator is in signaling contact with the nerve when it is positioned such that the signal can be effectively applied to the nerve. The apparatus is activated when the apparatus is in an operating state such that the signal will be applied as determined by the controller.

In certain such embodiments, a first stimulator is positioned in signaling contact with a left postganglionic ovary-innervating nerve of said patient to modulate the neural activity of said left nerve in the patient, and a second stimulator is positioned in signaling contact with a right postganglionic ovary-innervating nerve of said patient to modulate the neural activity of said right nerve in the patient. In certain such embodiments, the first and second stimulators are part of one apparatus according to the first aspect. In alternative such embodiments, the first and second stimulators are part of separate apparatuses according to the first aspect.

In one embodiment, the at least one stimulator in signaling contact with the nerve (or nerves) is shaped as a cuff for securing on the postganglionic ovary-innervating nerve. Cuffs as described—also referred to herein as cuff electrodes—may in certain embodiments be bipolar, tripolar, or quadripolar. A cuff electrode may have an external sheath that is wrapped around the cuff during implantation and is removed from the cuff prior to cuff removal in order to simplify debriding the cuff surface from fibrous connective capsule that forms chronically after implantation. A control unit can be either integrated with the electrodes or connected to them via flexible leads.

In certain embodiments, the postganglionic ovary-innervating nerve or nerves is/are the superior ovarian nerve or nerves, optionally also the ovarian plexus nerve or nerves. In a particular embodiment, the postganglionic ovary-innervating nerves are the left and right superior ovarian nerves.

Implementation of all aspects of the invention (as discussed both above and below) will be further appreciated by reference to FIGS. 2A-2C.

FIGS. 2A-2C show how the invention may be put into effect using one or more neuromodulation devices which are implanted in, located on, or otherwise disposed with respect to a patient 200 in order to carry out any of the various methods described herein. In this way, one or more neuromodulation devices can be used to treat PCOS in a patient, by modulating neural activity in at least one postganglionic ovary-innervating sympathetic nerve, for example a superior ovarian nerve, optionally also an ovarian plexus nerve (OPN).

In each of the FIGS. 2A-2C a separate neuromodulation device 100', 100" is provided in respect of each of the left and right ovaries, although as discussed above a device could be provided or used in respect of only one of the left and right ovaries. Each such neuromodulation device may be fully or partially implanted in the patient, or otherwise located, so as to provide neuromodulation of the respective nerve or nerves. FIG. 2A also shows schematically components of one of the neuromodulation devices 100, in which the device comprises several elements, components or functions grouped together in a single unit and implanted in the patient 200. A first such element is a stimulator 102 which is shown in proximity to a postganglionic ovary-innervating sympathetic nerve 90 of the patient. The stimulator 102 may be operated by a controller element 104. The device may comprise one or more further elements such as a communication element 106, a detector element 108, a power supply element 110 and so forth. Each of the left and right neuromodulation devices 100', 100" may operate independently, or may operate in communication with each other, for example using respective communication elements 106.

Each neuromodulation device 100', 100" may carry out the required neuromodulation independently, or in response to one or more control signals. Such a control signal may be provided by the controller 104 according to an algorithm, in response to output of one or more detector elements 108, and/or in response to communications from one or more external sources received using the communications element. As discussed herein, the detector element(s) could be responsive to a variety of different physiological and/or biochemical parameters.

FIG. 2B illustrates some ways in which the apparatus of FIG. 2A may be differently distributed. For example, in FIG. 2B the neuromodulation devices 100', 100" comprise stimulators 102 implanted proximally to a postganglionic ovary-innervating sympathetic nerve 90, but other elements such as a controller 104, a communication element 106 and a power supply 110 are implemented in a separate control unit 130 which may also be implanted in, or carried by the patient. The control unit 130 then controls the stimulators in both of the neuromodulation devices via connections 132 which may for example comprise electrical wires and/or optical fibres for delivering signals and/or power to the stimulators.

In the arrangement of FIG. 2B one or more detectors 108 are located separately from the control unit, although one or more such detectors could also or instead be located within the control unit 130 and/or in one or both of the neuromodulation devices 100', 100". The detectors may be used to detect one or more physiological and/or biochemical parameters of the patient, and the controller element or control unit then causes the stimulators to apply the signal in response to the detected parameter(s), for example only when a detected physiological and/or biochemical parameter meets or exceeds a predefined threshold value. Physiological and biochemical parameters which could be detected for such purposes include sympathetic tone (neural, hemodynamic (e.g. heart rate, blood pressure, heart rate variability) or circulating plasma/urine biomarkers), plasma nor-epinephrine concentration, plasma androgen concentration, plasma testosterone concentration, plasma gonadotrophin concentration, plasma FSH concentration, plasma LH concentration, plasma chorionic gonadotrophin concentration, plasma thyroid hormone concentration, plasma progesterone concentration. Similarly, a detected physiological parameter could be an action potential or pattern of action potentials in a nerve of the patient, for example a sympathetic nerve (e.g. a SON or OPN), wherein the action potential or pattern of action potentials is associated with PCOS.

A variety of other ways in which the various functional elements could be located and grouped into the neuromodulation devices, a control unit 130 and elsewhere are of course possible. For example, one or more sensors of FIG. 2B could be used in the arrangement of FIG. 2A or 2C or other arrangements.

FIG. 2C illustrates some ways in which some functionality of the apparatus of FIG. 2A or 2B is provided not implanted in the patient. For example, in FIG. 2C an external power supply 140 is provided which can provide power to implanted elements of the apparatus in ways familiar to the skilled person, and an external controller 150 provides part or all of the functionality of the controller 104, and/or provides other aspects of control of the apparatus, and/or provides data readout from the apparatus, and/or provides a data input facility 152. The data input facility could be used by a patient or other operator in various ways, for example to input data relating to the patient's ovarian cycle status.

Each neuromodulation device may be adapted to carry out the neuromodulation required using one or more physical modes of operation which typically involve applying a signal to a postganglionic ovary-innervating sympathetic nerve, such a signal typically involving a transfer of energy to (or from) the nerve(s). As already discussed, such modes may comprise modulating the nerve or nerves using an electrical signal, an optical signal, an ultrasound or other mechanical signal, a thermal signal, a magnetic or electromagnetic signal, or some other use of energy to carry out the required modulation. Such signals may be non-destructive signals. Such modulation may comprise increasing, inhibiting, blocking or otherwise changing the pattern of neural activity in the nerve or nerves. To this end, the stimulator 90 illustrated in FIG. 2A could be comprised of one or more electrodes, one or more photon sources, one or more ultrasound stimulators, one more sources of heat, or one or more other types of stimulator arranged to put the required neuromodulation into effect.

The neural modulation device(s) or apparatus may be arranged to inhibit neural activity of a postganglionic ovary-innervating sympathetic nerve (e.g. a SON and optionally also a OPN) by using the stimulator(s) to apply a voltage or current, for example a direct current (DC) such as a charge balanced direct current, or an AC waveform, or both. The device or apparatus may be arranged to use the stimulator(s) to apply a DC ramp, then apply a first AC waveform, wherein the amplitude of the waveform increases during the period the waveform is applied, and then apply a second AC waveform. The AC waveform(s) may have a frequency of 5 to 50 KHz, optionally 5-20 KHz, such as 5-10 or 10-20 KHz.

Thermal methods of neuromodulation typically manipulate the temperature of a nerve to inhibit signal propagation. For example, Patberg et al. (Blocking of impulse conduction in peripheral nerves by local cooling as a routine in animal experimentation. Journal of Neuroscience Methods 1984; 10:267-75, which is incorporated herein by reference) discuss how cooling a nerve blocks signal conduction without an onset response, the block being both reversible and fast acting, with onsets of up to tens of seconds. Heating the nerve can also be used to block conduction, and is generally easier to implement in a small implantable or localized stimulator or device, for example using infrared radiation from laser diode or a thermal heat source such as an electrically resistive element, which can be used to provide a fast, reversible, and spatially very localized heating effect (see for example Duke et al. J Neural Eng. 2012 June; 9(3):036003. Spatial and temporal variability in response to hybrid electro-optical stimulation, which is incorporated herein by reference). Either heating, or cooling, or both could be provided using a Peltier element.

Optogenetics is a technique that genetically modifies cells to express photosensitive features, which can then be activated with light to modulate cell function. Many different optogenetic tools have been developed that can be used to inhibit neural firing. A list of optogenetic tools to suppress neural activity has been compiled (Epilepsia. 2014 Oct. 9. doi: 10.1111/epi.12804. WONOEP appraisal: Optogenetic tools to suppress seizures and explore the mechanisms of epileptogenesis. Ritter L M et al., which is incorporated herein by reference). Acrylamine-azobenzene-quaternary ammonium (AAQ) is a photochromic ligand that blocks many types of $K_+$ channels and in the cis configuration, the relief of K+ channel block inhibits firing (Nat Neurosci. 2013 July; 16(7):816-23. doi: 10.1038/nn.3424. Optogenetic pharmacology for control of native neuronal signaling proteins.

Kramer R H et al, which is incorporated herein by reference). By adapting Channelrhodopsin-2 and introducing it into mammalian neurons with the lentivirus, it is possible to control inhibitory synaptic transmission (Boyden E S 2005). Instead of using an external light source such as a laser or light emitting diode, light can be generated internally by introducing a gene based on firefly luciferase (Land B B 2014). The internally generated light has been sufficient to generate inhibition.

Mechanical forms of neuromodulation can include the use of ultrasound which may conveniently be implemented using external instead of implanted ultrasound stimulators. Other forms of mechanical neuromodulation include the use of pressure (for example see "The effects of compression upon conduction in myelinated axons of the isolated frog sciatic nerve" by Robert Fern and P. J. Harrison Br. j. Anaesth. (1975), 47, 1123, which is incorporated herein by reference).

Some electrical forms of neuromodulation may use direct current (DC), or alternating current (AC) waveforms applied to a nerve using one or more electrodes. A DC block may be accomplished by gradually ramping up the DC waveform amplitude (Bhadra and Kilgore, IEEE Transactions on Neural systems and rehabilitation engineering, 2004 12(3) pp 313-324, which is incorporated herein by reference). Some AC techniques include KHFAC (kilohertz frequency AC) to provide a reversible block (for example see Kilgore and Bhadra, 2004, Medical and Biological Engineering and Computing, the content of which is incorporated herein by reference for all purposes). In the work of Kilgore and Bhadra, a proposed waveform was sinusoidal or rectangular at 3-5 kHz, and typical signal amplitudes that produced block were 3-5 Volts or 0.5 to 2.0 milliamperes peak to peak.

KHFAC may typically be applied at a frequency of between 1 and 50 kHz at a duty cycle of 100% (Bhadra, N. et al., Journal of Computational Neuroscience, 2007, 22(3), pp 313-326, which is incorporated herein by reference). Methods for selectively blocking activity of a nerve by application of a waveform having a frequency of 5-10 kHz are described in U.S. Pat. No. 7,389,145 (incorporated herein by reference). Similarly, U.S. Pat. No. 8,731,676 (incorporated herein by reference) describes a method of ameliorating sensory nerve pain by applying a 5-50 kHz frequency waveform to a nerve.

It is noted that neuromodulation by an electrical signal as described herein is not due to destructive thermal effects on the nerve, but rather due to the electrical signal per se.

Some commercially available nerve blocking systems include the Maestro® system available from Enteromedics Inc. of Minnesota, USA. Similar neuromodulation devices are more generally discussed in US2014/214129 and elsewhere.

The techniques discussed above principally relate to the blocking of neuronal activity. Where modulation by increasing activity or otherwise modifying activity in various ways is required, electrodes adjacent to or in contact with the nerve or particular parts of the nerve for example in contact with specific nerve fibers may be used to impart an electrical signal to stimulate activity in various ways, as would be appreciated by the skilled person.

In a third aspect, the invention provides a method of treating polycystic ovarian syndrome in a patient, the method comprising applying a signal to a part or all of a postganglionic ovary-innervating sympathetic nerve of said patient to modulate the neural activity of said nerve in the patient. In certain embodiments, the signal is applied to a superior ovarian nerve (SON) of the patient, optionally also a plexus nerve (OPN) of the patient to modulate the neural activity of the SON and optionally the OPN in the patient.

In certain embodiments, the signal is applied by a neuromodulation device comprising one or more stimulators configured to apply the signal. In certain preferred embodiments the neuromodulation device is at least partially implanted in the patient. In certain preferred embodiments, the neuromodulation device is wholly implanted in the patient.

As is known by the skilled person, mammals have a left and a right ovary, each ovary being innervated by postganglionic sympathetic nerves such as the superior ovarian nerve (SON) and ovarian plexus nerve (OPN) (FIG. 1). Each SON is associated with its respective ligament of ovary, whereas the plexus nerve runs inferior to the kidney and is associated with the ovarian artery (FIG. 1). Therefore, in certain embodiments, the signal can be applied directly to a part of or all of one or both SONs only, to modulate the neural activity in that or those SON(s). In an embodiment, one SON may be transected or ablated by another means (e.g. by a destructive signal), and the signal can be applied to the other SON. In certain embodiments the signal can be applied to a part of or all of one SON and one OPN, or both SONs and both OPNs in order to modulate the neural activity in the respective nerves.

In an embodiment, the signal is a destructive signal applied to the SON, such that transduction of action potentials by the SON is prevented even after the signal ceases. Destructive signals may include an ultrasonic, cryogenic or thermal signal, for example. Other destructive signals/ablative techniques are described in WO2013/134548.

In certain embodiments, treatment of PCOS is indicated by an improvement in a measurable physiological and/or biochemical parameter, for example an improvement in one or more of the symptoms of PCOS in the patient. That is, as a result of treatment, the patient exhibits one or more of: a reduction in sympathetic tone; a reduction in the appearance of polycystic ovaries (e.g. by gynaecological ultrasound); an increase in proportion of ovulatory menstrual cycles; a change in the concentration or release pattern of an androgen, for example, a reduction in androgen activity, for example a reduction in the concentration or release pattern of testosterone, such that the concentration or release pattern more closely resembles that of a healthy female individual, assuming the patient is exhibiting abnormal values for the respective parameter. In an embodiment, the patient may exhibit, as a result of treatment: a change in the concentration or release pattern of one or more gonadotrophin, for example follicle stimulating hormone (FSH), luteinizing hormone (LH), or chorionic gonadotrophin (CG), progesterone, and estrogen such that the concentration or release pattern more closely resembles that of a healthy female individual, assuming the patient is exhibiting abnormal values for the respective parameter.

Suitable methods for determining the value for any given parameter would be appreciated by the skilled person.

In certain embodiments, treatment of the condition is indicated by an improvement in the profile of neural activity in the nerve or nerves to which the signal is applied. That is, treatment of the condition is indicated by the neural activity in the nerve(s) approaching the neural activity in a fertile individual.

In certain embodiments the modulation in neural activity as a result of applying the signal is inhibition of neural activity in the nerve or nerves to which a signal is applied. That is, in such embodiments, application of the signal results in the neural activity in at least part of the nerve(s) being reduced compared to the baseline neural activity in that part of the nerve(s). Such a reduction in activity could equally be across the whole nerve(s), in which case neural activity would be reduced across the whole nerve(s). Therefore, in certain such embodiments, a result of applying the signal is at least partial inhibition of neural activity in the nerve or nerves. In certain embodiments, a result of applying the signal is full inhibition of neural activity in the nerve or nerves.

In certain embodiments, the modulation in neural activity as a result of applying the signal is a block on neural activity in the nerve or nerves to which a signal is applied. That is, in such embodiments, the application of the signal blocks action potentials from travelling beyond the point of the block in at least a part of the nerve(s). In certain such embodiments, the modulation is a partial block. In certain alternative embodiments, the modulation is a full block.

In certain embodiments, the modulation in neural activity as a result of applying the signal is an increase in neural activity in the nerve or nerves. That is, in such embodiments, application of the signal results in the neural activity in at least part of the nerve(s) being increased compared to the baseline neural activity in that part of the nerve. Such an increase in activity could equally be across the whole nerve, in which case neural activity would be increased across the whole nerve(s). Therefore, in certain such embodiments, a result of applying the signal is an increase in neural activity in the nerve(s). In certain embodiments, a result of applying the signal is an increase in neural activity across the whole nerve(s).

In certain embodiments, the modulation in neural activity as a result of applying the signal is an alteration to the pattern of action potentials in nerve or nerves to which a signal is applied. In certain such embodiments, the neural activity is modulated such that the resultant pattern of action potentials in the nerve or nerves resembles the pattern of action potentials in the nerve(s) observed in a subject without PCOS.

In certain embodiments, the signal is applied intermittently. In certain such embodiments, the signal is applied for a first time period, then stopped for a second time period, then reapplied for a third time period, then stopped for a fourth time period. In such an embodiment, the first, second, third and fourth periods run sequentially and consecutively. The series of first, second, third and fourth periods amounts to one application cycle. In certain such embodiments, multiple application cycles can run consecutively such that the signal is applied in phases, between which phases no signal is applied.

In such embodiments, the duration of the first, second, third and fourth time periods is independently selected. That is, the duration of each time period may be the same or different to any of the other time periods. In certain such embodiments, the duration of each of the first, second, third and fourth time periods is any time from 5 seconds (5 s) to 24 hours (24 h), 30 s to 12 h, 1 min to 12 h, 5 min to 8 h, 5 min to 6 h, 10 min to 6 h, 10 min to 4 h, 30 min to 4 h, 1 h to 4 h. In certain embodiments, the duration of each of the first, second, third and fourth time periods is 5 s, 10 s, 30 s, 60 s, 2 min, 5 min, 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h.

In certain embodiments wherein the signal is applied intermittently, the signal is applied for a specific amount of time per day. In certain such embodiments, the signal is applied for 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain such embodiments, the signal is applied continuously for the specified amount of time. In certain alternative such embodiments, the signal may be applied discontinuously across the day, provided the total time of application amounts to the specified time.

In certain embodiments wherein the signal is applied intermittently, the signal is applied only when the patient is in a specific state. In certain such embodiments, the signal is applied only when the patient is in a specific phase of the ovarian cycle. In certain such embodiments, the signal is applied only when the patient is in the follicular phase. Alternatively, the signal is applied only when the patient is in the luteal phase. In such embodiments, the status of the patient (e.g. that they are in a particular stage of the ovarian cycle) can be indicated by the patient. In alternative such embodiments, the status of the patient can be detected independently from any input from the patient. In certain embodiments in which the signal is applied by a neuromodulation device, the device further comprises a detector configured to detect the status of the patient, wherein the signal is applied only when the detector detects that the patient is in the specific state.

In certain embodiments of methods according to the invention, the method further comprises the step of detecting one or more physiological and/or biochemical parameters of the patient, wherein the signal is applied only when the detected physiological and/or biochemical parameter meets or exceeds a predefined threshold value. In such embodiments wherein more than one physiological and/or biochemical parameter is detected, the signal may be applied when any one of the detected parameters meets or exceeds its threshold value, alternatively only when all of the detected parameters meet or exceed their threshold values. In certain embodiments wherein the signal is applied by a neuromodulation device, the device further comprises at least one detector element configured to detect the one or more physiological and/or biochemical parameters.

In certain embodiments, the one or more detected physiological and/or biochemical parameters are one or more of the group consisting of: sympathetic tone (neural, hemodynamic (e.g. heart rate, blood pressure, heart rate variability) or circulating plasma/urine biomarkers), plasma nor-epinephrine concentration, plasma androgen concentration, plasma testosterone concentration, plasma gonadotrophin concentration, plasma FSH concentration, plasma LH concentration, plasma chorionic gonadotrophin concentration, plasma thyroid hormone concentration, plasma progesterone concentration In certain embodiments, the detected physiological parameter is an action potential or pattern of action potentials in a nerve of the patient, wherein the action potential or pattern of action potentials is associated with PCOS. In certain such embodiments, the nerve is a postganglionic ovary-innervating sympathetic nerve. In certain such embodiments, the nerve is an SON or OPN.

It will be appreciated that any two or more of the indicated physiological and/or biochemical parameters may be detected in parallel or consecutively. For example, in certain embodiments, the pattern of action potentials in the SON can be detected at the same time as plasma androgen concentration.

In certain alternative embodiments, the signal is permanently applied. That is, once begun, the signal is continuously applied to the nerve or nerves. It will be appreciated that in embodiments wherein the signal is a series of pulses, gaps between pulses do not mean the signal is not continuously applied.

In certain embodiments of the methods, the modulation in neural activity caused by the application of the signal (whether that is an increase, inhibition, block or other modulation of neural activity) is temporary. That is, upon cessation of the signal, neural activity in the nerve or nerves returns substantially towards baseline neural activity within 1-60 seconds, or within 1-60 minutes, or within 1-24 hours, optionally 1-12 hours, optionally 1-6 hours, optionally 1-4 hours, optionally 1-2 hours. In certain such embodiments, the neural activity returns substantially fully to baseline neural activity. That is, the neural activity following cessation of the signal is substantially the same as the neural activity prior to the signal being applied—i.e. prior to modulation.

In certain alternative embodiments, the modulation in neural activity caused by the application of the signal is substantially persistent. That is, upon cessation of the signal, neural activity in the nerve or nerves remains substantially the same as when the signal was being applied—i.e. the neural activity during and following modulation is substantially the same.

In certain embodiments, the modulation in neural activity caused by the application of the signal is partially corrective, preferably substantially corrective. That is, upon cessation of the signal, neural activity in the nerve or nerves more closely resembles the pattern of action potentials observed in a subject without PCOS than prior to modulation, preferably substantially fully resembles the pattern of action potentials observed in a female subject without PCOS. In such embodiments, the modulation caused by the signal can be any modulation as defined herein. For example, application of the signal may result in a block on neural activity, and upon cessation of the signal, the pattern of action potentials in the nerve or nerves resembles the pattern of action potentials observed in a subject without PCOS. By way of further example, application of the signal may result in modulation such that the neural activity resembles the pattern of action potentials observed in a subject without PCOS, and upon cessation of the signal, the pattern of action potentials in the nerve resembles the pattern of action potentials observed in a subject without PCOS. It is hypothesised that such a corrective effect is the result of a positive feedback loop.

In certain such embodiments, once first applied, the signal may be applied intermittently or permanently, as described in the embodiments above.

In certain embodiments, the signal is applied to a SON (and optionally a OPN) of said patient to modulate the neural activity said nerve or nerves in the patient.

In certain embodiments, the signal is applied bilaterally. That is, in such embodiments, the signal is applied to a postganglionic ovary-innervating sympathetic nerve on both the left and right side of the patient such that the neural activity is modulated in the nerves to which the signal is applied—i.e. the modulation is bilateral. In such embodiments, the signal applied to each nerve, and therefore the type and extent of modulation is independently selected from that applied to the other nerve or nerves. In certain embodiments the signal applied to the right nerve or nerves is the same as the signal applied to the left nerve or nerves. In certain alternative embodiments the signal applied to the right nerve or nerves is different to the signal applied to the left nerve or nerves. In certain preferred embodiments, a signal is applied to the left SON (and optionally left OPN) of the patient and a signal is applied to the right SON (and optionally right OPN) of the patient to modulate the neural activity of the left SON (and optionally the left OPN) and right SON (and optionally right OPN) of the patient.

In certain embodiments wherein the modulation is bilateral, each signal is applied by a neuromodulation device comprising one or more stimulators for applying the signal. In certain such embodiments, all signals are applied by the same neuromodulation device, that device have at least two stimulators, one to apply the signal to the left nerve(s) and one to apply the signal to the right nerve(s). In certain alternative embodiments, the each signal is applied by a separate neuromodulation device.

In certain embodiments, the signal applied is a non-destructive signal.

In certain embodiments of the methods according to the invention, the signal applied is an electrical signal, an electromagnetic signal (optionally an optical signal), a mechanical (optionally ultrasonic) signal, a thermal signal, a magnetic signal or any other type of signal.

In certain embodiments, the signal is not a thermal signal.

In certain such embodiments in which more than one signal may be applied, for example one to each SON (and optionally to one or both OPNs), each signal may be independently selected from an electrical signal, an optical signal, an ultrasonic signal, and a thermal signal. In those such embodiments in which two signals are applied by one modulation device, the two signals may be the same type of signal or may be different types of signal independently selected from an electrical signal, an optical signal, an ultrasonic signal, and a thermal signal. In those embodiments in which two signals are applied, each by a separate neuromodulation device, the two signals may be the same type of signal or may be different types of signal independently selected from an electrical signal, an optical signal, an ultrasonic signal, and a thermal signal.

In certain embodiments in which the signal is applied by a neuromodulation device comprising at least one stimulator, the stimulator may be comprised of one or more electrodes, one or more photon sources, one or more ultrasound stimulators, one more sources of heat, or one or more other types of stimulator arranged to put the signal into effect.

In certain embodiments, the signal is an electrical signal, for example a voltage or current. In certain such embodiments the signal comprises a direct current (DC) waveform, such as a charge balanced DC waveform, or an alternating current (AC) waveform, or both a DC and an AC waveform. In certain embodiments the signal comprises a DC ramp followed by a plateau and charge-balancing, followed by a first AC waveform, wherein the amplitude of the first AC waveform increases during the period in which the first AC waveform is applied, followed by a second AC waveform having a lower amplitude and/or lower frequency than the first AC waveform. In certain such embodiments, the DC ramp, first AC waveform and second AC waveform are applied substantially sequentially.

In certain embodiments in which the signal comprises one or more AC waveforms, at least one of the AC waveforms has a frequency of 1 to 50 kHz, optionally 5 to 50 KHz, optionally 5-20 KHz, such as 5-10 KHz or 10-20 KHz.

In certain embodiments wherein the signal is a thermal signal, the signal reduces the temperature of the nerve (i.e. cools the nerve). In certain alternative embodiments, the signal increases the temperature of the nerve (i.e. heats the nerve). In certain embodiments, the signal both heats and cools the nerve.

In certain embodiments wherein the signal is a mechanical signal, the signal is an ultrasonic signal. In certain alternative embodiments, the mechanical signal is a pressure signal.

Modulation of neural activity in the ovary-innervating sympathetic nerves results in the reappearance of ovarian estrous cycling and in a normalized ovarian morphological phenotype. Normal estrous cycling is driven by hormonal changes as well as neurological changes. These two systems operate together in parallel to regulate the ovarian and uterine cycle to increase the likelihood of successful conception. The interplay between these two factors in the fertility of a patient is set out in FIG. 3. The pharmacological approach is principally focused to restore the function of reproductive hypothalamus, whereas the neuromodulatory device is focused at the ovary levels. Therefore, it is expected to be particularly advantageous to combine the above-described neuromodulation devices and methods with endocrine fertility therapy in order to optimize or further increase the improvement in fertility of a subject. Examples of appropriate endocrine fertility therapies include administration of one or more pro-ovulation agents (for example clomiphene citrate, one or more gonadotrophins, gonadotrophin-releasing hormone), administration of progesterone and/or estrogen, and restoration of hypothalamic stimulation of the pituitary gland.

In a fifth aspect, the invention provides use of a neuromodulation device for treating polycystic ovarian syndrome in a patient by modulating neural activity in a postganglionic ovary-innervating sympathetic nerve of the patient.

In a preferred embodiment of all aspects of the invention, the subject or patient is a mammal, more preferably a human, more preferably a female human. In certain embodiments, the subject or patient is suffering from polycystic ovarian syndrome.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

EXAMPLES

Description of Methodology

Unless noted otherwise, the following provides a general outline of experimental procedures and protocols.

Female Sprague-Dawley rats randomly assigned to the following three groups:
  1 Control group: sham subcutaneous injection of 1 ml/kg sesame oil, no sham surgery;
  2 EV group: PCOS induced at the age of 28±3 days of age by a single subcutaneous injection of estradiol valerate (EV) at supra-physiological dose of 10 mg/kg, dissolved in 1 ml/kg sesame oil, surgery to remove right ovary;
  3 EV+ Block group: PCOS induced at the age of 28±3 days (as in group 2), surgery was performed to remove right ovary and implant the cuff electrode on the left SON, and superior ovarian nerve block was applied at 77±3 days of age for 21±3 days (3 animals) or at 88±2 days of age for 15±4 days (20 animals). Block was achieved with kilohertz frequency alternating current (KHFAC) applied as biphasic sinusoidal waveforms at 50 kHz and amplitude of ±1.5 mA.

Four primary outcome measures were evaluated in the animals:

Estrous cycle phase, evaluated daily by vaginal cytology;

Ovarian morphological phenotype, evaluated at 100±10 days of age using one half of dissected ovary embedded in paraffin, cut at 10-μm sections using the microtome, and stained with H&E to quantify the number of corpora lutea and cysts;

Norepinephrine concentration in ovary, evaluated at 100±10 days of age by high-performance liquid chromatography using second half of dissected ovary homogenized in 0.4 N perchloric acid;

Fertility, evaluated by performing assisted mating, establishing the presence of vaginal semen plug, and establishing pregnancy by presence of embryonic vesicles in the dissected uterine horns and uterine cavity at 7 days after a successful mating.

Further details of experimental procedures are described below.

Example 1

Generation of PCOS Rat Model

Estradiol valerate (EV) is a long lasting estradiol form. As described by Lara et al. (*Hypothalamic changes in neuroepinephrine release in rats with estradiol valerate-induced polycystic ovaries*, Biol. Reprod. 1995 (52): 398-404), the administration of a single pharmacological dose of EV blocks the reproductive hypothalamus and inhibits the cycling ovulatory activity characteristically seen in spontaneous ovulators. When this dose is administrated to prepubertal rats, it accelerates puberty and the rat loses the ability to ovulate in a cyclical manner. The rat does not reach and cyclic estrous activity (i.e. it does not ovulate) as determined by microscopically analysis of vaginal lavages. 60 days after the administration of EV the ovary present phenotypical characteristics of polycystic ovary represented by multiples follicular cyst and no corpus luteum (which is the result of ovulation). The condition is driven by an estradiol-induced hyperactivation of sympathetic nerves arriving to the ovary.

Example 2

Neuromodulatory Device

Cuff electrodes were custom-fabricated using precise laser patterning from silicone rubber (polydimethylsiloxane) and from embedded platinum foil layer (thickness of 12.5 μm) by Cortec GmbH. The inner cuff diameter was 0.5 mm to match the diameter of the SON. The stimulating cuff containing two electrode sites were connected (through a percutaneous connector) to an external pulse generator worn in a backpack. The stimulating cuff was used for inducing the conduction block in the SON with a kilohertz frequency alternating current (KHFAC).

Example 3

Implantation of the Neuromodulatory Device

Each cuff electrode was secured in place on the functioning SON using three sutures (in a rat which had been unilaterally transected on the opposing SON). FIG. 4 shows the cuff on the nerve before placing the sutures. Two methods for placing percutaneous connectors were used: on the dorsal skin and on the head. The dorsal skin placement was preferred for young subjects with a growing skull, while the head placement was preferred for adult subjects with fully grown skull. Two types of sutures were used: absorbable (PDS) and non-absorbable (monofilament Nylon). The absorbable suture was preferred for long-term implantation time (more than 2 months), while non-absorbable suture was preferred for short-term implantation time (less than 2 months). For closing the skin incision above the cuff electrode implant, we used a continuous subcutaneous suturing technique followed by an application of veterinary cyanoacrylate glue (Dermabond) in order to improve the cosmesis and prevent the subject from accidentally removing the suture.

Example 4

Evaluation of the Functionality of Implanted Electrodes

To confirm that the implanted cuff electrodes remain functional, we performed weekly measurements of electrochemical and electroneural performance. Electrochemical performance was evaluated by measuring the electrode impedance at multiple frequencies (from 1 Hz to 100 kHz) using a potentiostat (PGSTAT302N, Metrohm A G) and electrochemical software (NOVA, Metrohm A G). Of particular interest to us was the impedance at 50 kHz, since the stimulation to the nerve was applied at that frequency. FIG. 5 shows the representative electrochemical impedances implanted with SON cuff electrodes for 2 months. Electroneural performance was evaluated using a custom headstage (<1 μV RMS input noise, 200 Hz one-pole high-pass filter, 50× gain, DC-coupled, Plexon Inc), data acquisition hardware (PXI-4461, National Instruments), and custom software written in Visual Basic 6.0 (Microsoft Inc.). Persistence of spontaneous neural activity in the SON indicated the functionality of the cuff and viability of the nerve (FIG. 6).

Example 5

Impact of KHFAC Block on Ovarian Morphological Phenotype

Stimulating cuffs were used for inducing the conduction block in the SON with the kilohertz frequency alternating current (KHFAC). The KHFAC was continuously applied (24 hours a day) using a bipolar current-controlled sinusoid at a frequency of 50 kHz. The KHFAC amplitude of 1.5 mA was used to fully block the nerve conduction. Dissected rat ovary was formaldehyde-fixed, embedded in paraffin, and cut at 6-10 μm sections using the microtome. The H&E histological staining was used to quantify the ovarian phenotype, Evaluation of ovarian phenotype was performed at 77±3 days of age (FIGS. 7 and 8). FIG. 7A illustrates a typical ovarian appearance in untreated rats, while FIG. 7B illustrates the changes in morphology 50 days after the injection of Estradiol Valerate. The number of healthy follicles was reduced after the EV treatment but not after EV treatment plus KHFAC for 21±3 days (FIG. 8A). The number of corpora lutea was increased after EV treatment plus KHFAC for 21±3 days (FIG. 8B). The number of cysts was increased after the EV treatment but not after EV treatment plus KHFAC for 21±3 days (FIG. 8C).

In another study, the surgery was performed in 11 EV treated rats to remove right ovary and implant the cuff electrode on the left SON, followed by KHFAC for 15±4 days, and removal of right ovary. Within animal comparison of ovarian morphological phenotype demonstrated a general trend toward decreased number of corpora lutea after KHFAC, when comparing the left ovary (7.3±0.8) and the right ovary subjected to KHFAC (12.4±2.1) (FIG. 9). Averages are shown as gray line on the figure.

Example 6

Impact of KHFAC Block on Norepinephrine (NE) Concentration in the Ovary

Evaluation of Norepinephrine (NE) concentration in ovary (normalized by the ovary weight) indicated that highest NE level was present in the EV group (336±19 pg/mg ovary), followed by the control group (232±22 pg/mg ovary) and the EV+ Block group (71±13 pg/mg ovary). These differences among the groups were highly significant ($p<0.001$, based on AVOVA), indicating dramatic suppression of NE release due to a KHFAC block of the SON continuously applied at 50 kHz and amplitude of ±1.5 mA (FIG. 10).

Example 7

Impact of KHFAC Block on Ovarian Estrous Cycling

Continuous application of KHFAC block for 21±3 days in three EV-treated animals resulted in reappearance of ovarian estrous cycles (FIG. 11). Estrous cycling was determined by evaluating the morphology of cells obtained from vaginal lavages and classified into: proestrus (P)—day before ovulation, estrus (E) day after ovulation, and metestrus (M)—stage in which the follicle is growing and preparing for the next ovulation. After 30 days after EV injections, rats stopped cycling (i.e. became anovulatory). Then, at 7 to 17 days after the initiation of KHFAC block, animals restored normal estrous cycling.

Example 8

Impact of KHFAC Block on Fertility

Application of chronic KHFAC block in the EV+ Block group did not produce any detrimental effects on fertility, as the percentage of pregnant animals was the same in the EV-treated animals (54±14%) and EV-treated and HF-blocked animals (58±15%) (FIG. 12). Fertility was evaluated by performing assisted mating, establishing the presence of vaginal semen plug, and establishing pregnancy by a presence of embryonic vesicles in the dissected uterine horns and uterine cavity at 7 days after a successful mating.

The invention claimed is:

1. A method of treating polycystic ovarian syndrome in a patient, the method comprising applying an electrical current by a neuromodulation device comprising one or more stimulators configured to be secured on a postganglionic ovary-innervating nerve and configured to apply the electrical current to a part or all of the postganglionic ovary-innervating sympathetic nerve of said patient to modulate neural activity of said nerve in the patient,
wherein at least one stimulator of the one or more stimulators is shaped as a cuff, wherein applying the electrical current to a part or all of the postganglionic ovary-innervating sympathetic nerve of said patient to modulate the neural activity of said nerve in the patient comprises the steps of:
(i) applying a direct current (DC) ramp followed by a plateau and charge-balancing;
(ii) applying a first alternating current (AC) waveform, wherein the first AC waveform has an amplitude and is applied for a period, wherein the amplitude of the waveform increases during the period the waveform is applied; and
(iii) applying a second AC waveform having a lower amplitude and/or a lower frequency than the first AC waveform.

* * * * *